US006809189B2

(12) United States Patent
Noteborn et al.

(10) Patent No.: US 6,809,189 B2
(45) Date of Patent: Oct. 26, 2004

(54) APOPTIN-ASSOCIATING PROTEIN

(75) Inventors: Mathieu Hubertus M. Noteborn, Leiderdorp (NL); Astrid Adriana A. M. Danen-van Oorschot, Berkel en Rodenrijs (NL); Jennifer Leigh Rohn, Amsterdam (NL); Bertram Weiss, Berlin (DE)

(73) Assignee: Leadd B.V., Leiden (NL)

( * ) Notice: Subject to any disclaimer, the term of this patent is extended or adjusted under 35 U.S.C. 154(b) by 0 days.

(21) Appl. No.: 09/764,176

(22) Filed: Jan. 17, 2001

(65) Prior Publication Data

US 2002/0127553 A1 Sep. 12, 2002

(30) Foreign Application Priority Data

Jan. 17, 2000 (EP) ............................................. 00200169
Apr. 7, 2000 (EP) ............................................. 00250118

(51) Int. Cl.[7] ......................... C07H 21/04; C12N 15/74; C12N 5/02; C12N 1/20
(52) U.S. Cl. .................. 536/23.1; 536/23.5; 435/320.1; 435/325; 435/366; 435/252.3
(58) Field of Search ............................... 536/23.5, 23.1; 435/320.1, 325, 366, 252.3, 254.11; 514/44

(56) References Cited

U.S. PATENT DOCUMENTS 5,981,205 A * 11/1999 Hemmings et al. ............ 435/15

FOREIGN PATENT DOCUMENTS

| EP | 0 921 192 A1 | 6/1999 |
| EP | 0 924 296 A2 | 6/1999 |
| WO | WO 99/53040 | * 10/1999 |

OTHER PUBLICATIONS

Benet et al., pp. 3–32, in The Pharmacological Basis of Therapeutics, 8th ed., McGraw–Hill, Inc., New York, 1990.*
Jain et al., Cancer and Metastasis Reviews 9:253–266, 1990.*
Jain R.K, Science, 271:1079–1080, 1996.*
Dermer, Biotechnology 12:320, 1994.*
Database GenEmbl on GenCore version 4.5, Accession No. AX015052, Oct. 1999.*
Noteborn et al. Drug Resistance Updates 1:99–103, 1998.*
Strausberg R. Database EST on GenCore version 4.5, Accession No. BE746443, Sep. 2000.*
Van Oorschot et al. (pp. 245–249 in Drug Resistance in Leukemia and Lymphoma III, ed. Kaspers et al., Kluwer Academic/Plenum Publishers, New York, 1999.*

Noteborn et al (Biogenic Amines, 1998, 15:73–91).*
Abstract XP–002140967, May 1999.
Abstract XP–002140968., May 1995.
Abstract XP–002140969., 2000.
Danen–van Oorschot et al., "Apoptin induces apoptosis in human transformed and malignant cells but not in normal cells", *Proc. Natl. Acad. Sci. USA*, vol. 94, pp. 5843–5847, May 1997.
Danen–van Oorschot et al., "BAG–1 inhibits p53–induced but not apoptin–induced apoptosis", *Apoptosis*, vol. 2, No. 4, pp. 395–402, 1997.
Jacobson et al., "Modifying chromatin and concepts of cancer", *Chromosomes and expression mechanisms*, pp. 175–184.
Lu et al., "A Novel Gene (PLU–1) Containing Highly Conserved Putative DNA/Chromatin Binding Motifs Is Specifically Up–regulated in Breast Cancer", *The Journal of Biological Chemistry*, vol. 274, No. 22, pp. 15633–15645, 1999.
McDonnell et al., "Implications of apoptotic cell death regulation in cancer therapy", *Cancer Biology*, vol. 6, pp. 53–60, 1995.
Mullersman et al., "The PHD finger: implications for chromatin–mediated transcriptional regulation", *TIBS* 20, pp. 56–59, Feb. 1995.
Noteborn et al., "Characterization of Cloned Chicken Anemia Virus DNA That Contains All Elements for the Infectious Replication Cycle", *Journal of Virology*, vol. 65, No. 6, pp. 3131–3139, Jun. 1991.
Noteborn et al., "Chicken Anemia Virus: Induction of Apoptosis by a Single Protein of a Single–Stranded DNA Virus", *Virology*, vol. 8, Article No. V1980154, pp. 497–504, 1998.
Pietersen et al., "Specific tumor–cell killing with adenovirus vectors containing the apoptin gene", *Gene Therapy*, vol. 6, pp. 882–892, 1999.
Zhuang et al., "Apoptin, a Protein Derived from Chicken Anemia Virus, Induces p53–independent Apoptosis in Human Osteosarcoma Cells", *Cancer Research*, vol. 55, pp. 486–489, Feb. 1, 1995.
Zhuang et al., "Apoptin, a Protein Encoded by Chicken Anemia Virus, Induces Cell Death in Various Human Hematologic Malignant Cells in vitro", *Leukemia*, vol. 9, Suppl. 1, pp. S118–S120, 1995.

* cited by examiner

*Primary Examiner*—Susan Ungar
(74) *Attorney, Agent, or Firm*—TraskBritt

(57) ABSTRACT

The invention relates to the field of apoptosis. The invention provides novel therapeautic possibilities, for example, novel combinatorial therapies or novel therapeutic compounds that can work alone, sequentially to, or jointly with Apoptin, especially in those cases wherein p53 is (partly) nonfunctional.

10 Claims, 17 Drawing Sheets

Figure 1

```
1    CCCAGACCTC TGGCATAGAG GAGCCTTCTG AGACAAAGGG TTCTATGCAA
51   AAAAGCAAAT TCAAATATAA GTTGGTTCCT GAAGAAGAAA CCACTGCCTC
52   AGAAAATACA GAGATAACCT CTGAAAGGCA GAAAGAGGGC ATCAAATTAA
53
54   CAATCAGGAT ATCAAGTCGG AAAAAGAAGC CCGATTCTCC CCCCAAAGTT
55
56   CTAGAACCAG AAAACAAGCA AGAGAAGACA GAAAAGGAAG AGGAGAAAAC
57
58   AAATGTGGGT CGTACTTTAA GAAGATCTCC AAGAATATCT AGACCCACTG
59
60   CAAAGGTGGC TGAGATCAGA GATCAGAAAG CTGATAAAAA AAGAGGGGAA
61
62   GGAGAAGATG AGGTGGAAGA AGAGTCAACA GCTTTGCAAA AAACTGACAA
63
64   AAAGGAAATT TTGAAAAAAT CAGAGAAAGA TACAAATTCT AAAGTAAGCA
65
66   AGGTAAAACC CAAAGGCAAA GTTCGATGGA CTGGTTCTCG GACACGTGGC
67
68   AGATGGAAAT ATTCCAGCAA TGATGAAAGT GAAGGGTCTG GCAGTGAAAA
69
70   ATCATCTGCA GCTTCAGAAG AGGAGGAGGA AAAGGAAAGT GAAGAAGCCA
71
72   TCCTAGCAGA TGATGATGAA CCATGCAAAA AATGTGGCCT TCCAAACCAT
73
74   CCTGAGCTAA TTCTTCTGTG TGACTCTTGC GATAGTGGAT ACCATACTGC
75
76   CTGCCTTCGC CCTCCTCTGA TGATCATCCC AGATGGAGAA TGGTTCTGCC
77
78   CACCTTGCCA ACATAAACTG CTCTGTGAAA AATTAGAGGA ACAGTTGCAG
79
80   GATTTGGATG TTGCCTTAAA GAAGAAAGAG CGTGCCGAAC GAAGAAAAGA
81
82   ACGCTTGGTG TATGTTGGTA TCA (SEQ. ID NO. 1)
```

Figure 2

```
   1  CCTTTTCTTG ATAAGGACGC ACAAAGATTG AGTCCAATAC CAGAAGAAGT
  51  TCCAAAGAGT ACTCTAGAGT CAGAAAAGCC TGGCTCTCCT GAGGCAGCTG
 101  AAACTTCTCC ACCATCTAAT ATCATTGACC ACTGTGAGAA ACTAGCCTCA
 151  GAAAAGAAG  TGGTAGAATG CCAGAGTACA AGTACTGTTG GTGGCCAGTC
 201  TGTGAAAAAA GTAGACCTAG AAACCCTAAA AGAGGATTCT GAGTTCACAA
 251  AGGTAGAAAT GGATAATCTG ACAATGCCC  AGACCTCTGG CATAGAGGAG
 301  CCTTCTGAGA CAAAGGGTTC TATGCAAAAA AGCAAATTCA AATATAAGTT
 351  GGTTCCTGAA GAAGAAACCA CTGCCTCAGA AAATACAGAG ATAACCTCTG
 401  AAAGGCAGAA AGAGGGCATC AAATTAACAA TCAGGATATC AAGTCGGAAA
 451  AAGAAGCCCG ATTCTCCCCC CAAAGTTCTA GAACCAGAAA ACAAGCAAGA
 501  GAAGACAGAA AAGGAAGAGG AGAAAACAAA TGTGGGTCGT ACTTTAAGAA
 551  GATCTCCAAG AATATCTAGA CCCACTGCAA AGGTGGCTGA GATCAGAGAT
 601  CAGAAAGCTG ATAAAAAAAG AGGGGAAGGA GAAGATGAGG TGGAAGAAGA
 651  GTCAACAGCT TTGCAAAAAA CTGACAAAAA GGAAATTTTG AAAAAATCAG
 701  AGAAAGATAC AAATTCTAAA GTAAGCAAGG TAAAACCCAA AGGCAAAGTT
 751  CGATGGACTG GTTCTCGGAC ACGTGGCAGA TGGAAATATT CCAGCAATGA
 801  TGAAAGTGAA GGGTCTGGCA GTGAAAAATC ATCTGCAGCT TCAGAAGAGG
 851  AGGAGGAAAA GGAAAGTGAA GAAGCCATCC TAGCAGATGA TGATGAACCA
 901  TGCAAAAAAT GTGGCCTTCC AAACCATCCT GAGCTAATTC TTCTGTGTGA
 951  CTCTTGCGAT AGTGGATACC ATACTGCCTG CCTTCGCCCT CCTCTGATGA
1001  TCATCCCAGA TGGAGAATGG TTCTGCCCAC CTTGCCAACA TAAACTGCTC
1051  TGTGAAAAAT TAGAGGAACA GTTGCAGGAT TTGGATGTTG CCTTAAAGAA
1101  GAAAGAGCGT GCCGAACGAA GAAAAGAACG CTTGGTGTAT GTTGGTATCA
(SEQ ID NO. 2)
```

Figure 3

```
  1  HEGPFLDKDA QRLSPIPEEV PKSTLESEKP GSPEAAETSP

41  PSNIIDHCEK LASEKEVVEC QSTSTVGGQS VKKVDLETLK

81  EDSEFTKVEM DNLDNAQTSG IEEPSETKGS MQKSKFKYKL

121  VPEEETTASE NTEITSERQK EGIKLTIRIS SRKKKPDSPP

161  KVLEPENKQE KTEKEEEKTN VGRTLRRSPK ISRPTAKVAE

201  IRDQKADKKR GEGEDEVEEE STALQKTDKK EILKKSEKDT

202NSKVSKVKPK GKVRWTGSRT RGRWKYSSND ESEGSGSEKS

281  SAASEEEEK ESEEAILADD DEPCKKCGLP NHPELILLCD

321  SCDSGYHTAC LRPPLMIIPD GEWFCPPCQH KLLCEKLEEQ

361  LQDLDVALKK KERAERRKER LVYVGI    (SEQ. ID NO. 3)
```

Figure 4

AAP-2 and/or apoptin induce apoptosis in human tumor cells.

Apoptosis activity in Saos-2 cells

|        | Synthesised Proteins |       |         |               |
|--------|------|-------|---------|---------------|
|        | LacZ | AAP-2 | Apoptin | AAP-2/Apoptin |
| Exp. 1 | -    | +     | ++      | +++           |
| Exp. 2 | -    | +     | ++      | +++           |
| Exp. 3 | -    | +     | ++      | +++           |

Figure 5

```
1    CCGATGGTAG GCGGCGGCGG GGTCGGCGGC GGCCTCCTGG AGAATGCCAA
51   CCCCCTCATC TACCAGCGCT CTGGGGAGCG GCCTGTGACG GCAGGCGAGG
101  AGGACGAGCA GGTTCCCGAC AGCATCGACG CACGCGAGAT CTTCGARCTG
151  ATTCGCTCCA TCAATGACCC GGAGCATCCA CTGACGCTAG AGGAGTTGAA
201  CGTAGTAGAG CAGGTGCGGG TTCAGGTTAG CGACCCCGAG AGTACAGTGG
251  CTGTGGCTTT CACACCAACC ATTCCGCACT GCAGCATGGC CACCCTTATT
301  GGTCTGTCCA TCAAGGTCAA GCTTCTGCGC TCCCTTCCTC AGCGTTTCAA
351  GATGGACGTG CACATTACTC CGGGGACCCA TGCCTCAGAG CATGCAGTGA
401  ACAAGCAACT TGCAGATAAG GAGCGGGTGG CAGCTGCCCT GGAGAACACC
451  CACCTCTTGG AGGTTGTGAA TCAGTGCCTG TCAGCCCGCT CCTGAGCCTG
501  GCCTTTGACC CCTCAACCTG CATACTGGGT ATCCTGGTCC CAACTCCTGC
551  CAAGGGCTGT TACCGTTGTT TTCCTGGAAT CACTCACAAA TGAGAAACTA
601  ACATTTGCCT TTTTGTAATA AAGTTAATTT ATATTCAAAA AAAAAAAAA
651  C    (SEQ. ID NO. 4)
```

Figure 6

```
1   HEGPMVGGGG VGGGLLENAN PLIYQRSGER PVTAGEEDEQ

41  VPDSIDAREI FDLIRSINDP EHPLTLEELN VVEQVRVQVS

81  DPESTVAVAF TPTIPHCSMA TLIGLSIKVK LLRSLPQRFK

121 MDVHITPGTH ASEHAVNKQL ADKERVAAAL ENTHLLEVVN

161QCLSARS   (SEQ. ID NO. 5)
```

Figure 7A

```
   1  GGCAAGCCCG AAGGGAAGGA GAGAAGGGGG CGGAAAGAGG GCGGAAAGTG
  51  AAAGGCGCCG AGGGCCGCTC TGTCTCCCGT CTGACTCGGT TCTCGACTGC
 101  TCCGGGCCGC CGATGTATTG TGGGATCGCG GACCGTCCCT GAGACGCTGG
 151  GATCCGCAGA GGAGCCCACT TGAGAGCGCC TCCTGTCGTC TGTAAGGTTG
 201  CCTTGCCATC CCTCGGCACC CCAACTTCCC CCGCCCCCCC ATCGCCTCCT
 251  CCTCCATCCT CCAGTTCAGG CGGCGCAGGG CGGCGGCACG GCGGCGGTGA
 301  TGGCTCCTCC GGGCTGCCCG GGTTCGTGCC CCAACTTCGC CGTAGTCTGC
 351  TCCTTCTTGG AGCGCTACGG GCCGCTGCTA GACCTGCCTG AGTTGCCGTT
 401  CCCTGAGCTG GAGCGGGTGC TGCAGGCGCC GCCGCCGGAC GTCGGCAACG
 451  GAGAAGTACC AAAAGAATTG GTGGAGCTCC ATTTGAAGCT GATGAGGAAA
 501  ATTGGCAAAT CTGTTACTGC AGACAGATGG GAAAAATATT TGATCAAGTA
 551  CCTCTGTGAG TGTCAGTTTG ATGACAATCT CAAATTCAAG AATATTATTA
 601  ATGAGGAGGA TGCCGATACT ATGCGTCTCC AGCCAATTGG TCGAGACAAA
 651  GATGGCCTCA TGTACTGGTA CCAATTGGAT CAAGATCACA ATGTCAGAAT
 701  GTACATAGAA GAACAAGATG ATCAAGATGG CTCTTCATGG AAATGCATTG
 751  TCAGAAATCG AAACGAGTTG GCTGAGACTC TTGCACTCCT GAAAGCACAA
 801  ATTGATCCTG TACTATTGAA AAACTCTAGC CAACAAGACA ACTCTTCTCG
 851  GGAAAGTCCC AGCTTAGAGG ATGAGGAGAC TAAAAAAGAG GAAGAAACAC
 901  CTAAACAAGA GGAACAGAAA GAAAGTGAAA AGATGAAAAG TGAGGAGCAG
 951  CCTATGGATT TAGAAAACCG TTCTACAGCC AATGTTCTAG AAGAGACTAC
1001  TGTGAAAAAA GAAAAAGAAG ATGAAAAGGA ACTTGTGAAA CTGCCAGTCA
1051  TAGTGAAGCT AGAAAAACCT TTGCCAGAAA ATGAAGAAAA AAAGATTATC
1101  AAAGAAGAAA GTGATTCCTT CAAGGAAAAT GTCAAACCCA TTAAAGTTGA
1151  GGTGAAGGAA TGTAGAGCAG ATCCTAAAGA TACCAAAAGT AGCATGGAGA
1201  AGCCAGTGGC ACAGGAGCCT GAAAGGATCG AATTTGGTGG CAATATTAAA
1251  TCTTCTCACG AAATTACTGA GAAATCTACT GAAGAAACTG AGAAACTTAA
1301  AAATGACCAG CAGGCCAAGA TACCACTAAA AAAACGAGAA ATTAAACTGA
1351     GTGATGATTT TGACAGTCCA GTCAAGGGAC CTTTGTGTAA ATCAGTTACT
```

Figure 7B

```
1401  CCAACAAAAG AGTTTTTGAA AGATGAAATA AAACAAGAGG AAGAGACTTG
1451  TAAAAGGATC TCTACAATCA CTGCTTTGGG TCATGAAGGG AAACAGCTGG
1501  TAAATGGAGA AGTTAGTGAT GAAAGGGTAG CTCCAAATTT TAAGACAGAA
1551  CCAATAGAGA CAAAGTTTTA TGAGACAAAG GAAGAGAGCT ATAGCCCCTC
1601  TAAGGACAGA AATATCATCA CGGAGGGAAA TGGAACAGAG TCCTTAAATT
1651  CTGTCATAAC AAGTATGAAA ACAGGTGAGC TTGAGAAAGA AACAGCCCCT
1701  TTGAGGAAAG ATGCAGATAG TTCAATATCA GTCTTAGAGA TCCATAGTCA
1751  AAAAGCACAA ATAGAGGAAC CCGATCCTCC AGAAATGGAA ACTTCTCTTG
1801  ATTCTTCTGA GATGGCAAAA GATCTCTCTT CAAAAACTGC TTTATCTTCC
1851  ACCGAGTCGT GTACCATGAA AGGTGAAGAG AAGTCTCCCA AAACTAAGAA
1901  GGATAAGCGC CCACCAATCC TAGAATGTCT TGAAAAGTTA GAGAAGTCCA
1951  AAAAGACTTT TCTTGATAAG GACGCACAAA GATTGAGTCC AATACCAGAA
2001  GAAGTTCCAA AGAGTACTCT AGAGTCAGAA AAGCCTGGCT CTCCTGAGGC
2051  AGCTGAAACT TCTCCACCAT CTAATATCAT TGACCACTGT GAGAAACTAG
2101  CCTCAGAAAA AGAAGTGGTA GAATGCCAGA GTACAAGTAC TGTTGGTGGC
2151  CAGTCTGTGA AAAAGTAGA CCTAGAAACC CTAAAAGAGG ATTCTGAGTT
2201  CACAAAGGTA GAAATGGATA ATCTGGACAA TGCCCAGACC TCTGGCATAG
2251  AGGAGCCTTC TGAGACAAAG GGTTCTATGC AAAAAAGCAA ATTCAAATAT
2301  AAGTTGGTTC CTGAAGAAGA AACCACTGCC TCAGAAAATA CAGAGATAAC
2351  CTCTGAAAGG CAGAAAGAGG GCATCAAATT AACAATCAGG ATATCAAGTC
2401  GGAAAAAGAA GCCCGATTCT CCCCCCAAAG TTCTAGAACC AGAAAACAAG
2451  CAAGAGAAGA CAGAAAAGGA AGAGGAGAAA ACAAATGTGG GTCGTACTTT
2501  AAGAAGATCT CCAAGAATAT CTAGACCCAC TGCAAAAGTG GCTGAGATCA
2551  GAGATCAGAA AGCTGATAAA AAAAGAGGGG AAGGAGAAGA TGAGGTGGAA
2601  GAAGAGTCAA CAGCTTTGCA AAAAACTGAC AAAAAGGAAA TTTTGAAAAA
2651  ATCAGAGAAA GATACAAATT CTAAAGTAAG CAAGGTAAAA CCCAAAGGCA
2701  AAGTTCGATG GACTGGTTCT CGGACACGTG GCAGATGGAA ATATTCCAGC
2751  AATGATGAAA GTGAAGGGTC TGGCAGTGAA AAATCATCTG CAGCTTCAGA
2801  AGAGGAGGAA GAAAAGGAAA GTGAAGAAGC CATCCTAGCA GATGATGATG
```

Figure 7C

```
2851  AACCATGCAA AAAATGTGGC CTTCCAAACC ATCCTGAGCT AATTCTTCTG
2901  TGTGACTCTT GCGATAGTGG ATACCATACT GCCTGCCTTC GCCCTCCTCT
2951  GATGATCATC CCAGATGGAG AATGGTTCTG CCCACCTTGC CAACATAAAC
3001  TGCTCTGTGA AAAATTAGAG GAACAGTTGC AGGATTTGGA TGTTGCCTTA
3051  AAGAAGAAAG AGCGTGCCGA ACGAAGAAAA GAACGCTTGG TGTATGTTGG
3101  TATCAGTATT GAAAACATCA TTCCTCCACA AGAGCCAGAC TTTTCTGAAG
3151  ATCAAGAAGA AAAGAAAAAA GATTCAAAAA AATCCAAAGC AAACTTGCTT
3201  GAAAGGAGGT CAACAAGAAC AAGGAAATGT ATAAGCTACA GATTTGATGA
3251  GTTTGATGAA GCAATTGATG AAGCTATTGA AGATGACATC AAAGAAGCCG
3301  ATGGAGGAGG AGTTGGCCGA GGAAAAGATA TCTCCACCAT CACAGGTCAT
3351  CGTGGGAAAG ACATCTCTAC TATTTTGGAT GAAGAAAGAA AAGAAAATAA
3401  ACGACCCCAG AGGGCAGCTG CTGCTCGAAG GAAGAAACGC CGGCGATTAA
3451  ATGATCTGGA CAGTGATAGC AACCTGGATG AAGAAGAGAG CGAGGATGAA
3501  TTCAAGATCA GTGATGGATC TCAAGATGAG TTTGTTGTGT CTGATGAAAA
3551  CCCAGATGAA AGTGAAGAAG ATCCGCCATC TAATGATGAC AGTGACACTG
3601  ACTTTTGTAG CCGTAGACTG AGGCGACACC CCTCTCGGCC AATGAGGCAG
3651  AGCAGGCGTT TGCGAAGAAA GACCCCAAAG AAAAAATATT CCGATGATGA
3701  TGAAGAGGAG GAATCTGAGG AGAATAGTAG AGACTCTGAA AGTGACTTCA
3751  GTGATGATTT TAGTGATGAT TTTGTAGAAA CTCGGCGAAG GCGGTCAAGG
3801  AGAAATCAGA AAAGACAAAT TAACTACAAA GAAGACTCAG AAAGTGACGG
3851
3901  GAAGACTTTC CAGCTCAGAG AGTGAAGAGA GCTATTTGTC CAAGAACTCT
3951  GAAGATGATG AGCTAGCTAA AGAATCAAAG CGGTCAGTTC GAAAGCGGGG
4001  CCGAAGCACA GACGAGTATT CAGAAGCAGA TGAGGAGGAG GAGGAAGAGG
4051  AAGGCAAACC ATCCCGCAAA CGGCTACACC GGATTGAGAC GGATGAGGAG
4101  GAGAGTTGTG ACAATGCTCA TGGAGATGCA AATCAGCCTG CCCGTGACAG
4151  CCAGCCTAGG GTCCTGCCCT CAGAACAAGA GAGCACCAAG AAGCCCTACC
4201  GGATAGAAAG TGATGAGGAA GAGGACTTTG AAAATGTAGG CAAAGTGGGG
4251  AGCCCATTGG ACTATAGCTT AGTGGACTTA CCTTCAACCA ATGGACAGAG
4301  CCCTGGCAAA GCCATTGAGA ACTTGATTGG CAAGCCTACT GAGAAGTCTC
4351  AGACCCCCAA GGACAACAGC ACAGCCAGTG CAAGCCTAGC CTCCAATGGG
```

Figure 7D

```
4401  ACAAGTGGTG GGCAGGAGGC AGGAGCACCA GAAGAGGAGG AAGATGAGCT
4451  TTTGAGAGTG ACTGACCTTG TTGATTATGT CTGTAACAGT GAACAGTTAT
4501  AAGACTTTTT TTCCATTTTT GTGCTAATTT ATTCCACGGT AGCTCTCACA
4551  CCAGCGGGCC AGTTATTAAA AGCTGTTTAA TTTTTCCTAG AAAACTCCAC
4601  TACAGAATGA CTTTTAGAAG AAAAATTTCA ACAAATCCTG AAGTCTTTCT
4651  GTGAAGTGAC CAGTTCTGAA CTTTGAAGAT AAATAATTGC TGTAAATTCC
4701  TTTTGATTTT CTTTTTCCAG GTTCATGGTC CTTGGTAATT TCATTCATGG
4751  AAAAAAATCT TATTATAATA ACAACAAAGA TTTGTATATT TTTGACTTTA
4801  TATTTCCTGA GCTCTCCTGA CTTTGTGAAA AAGGGTGGAT GAAAATGCAT
4851  TCCGAATCTG TGAGGGCCCA AAACAGAATT TAGGGGTGGG TGAAAGCACT
4901  TGTGCTTTAG CTTTTTCATA TTAAATATAT ATTATATTTA AACATTCATG
4951  GCATAGATGA TGATTTACAG ACAATTTAAA AGTTCAAGTC TGTACTGTTA
5001  CAGTTTGAGA ATTGTAGATA ACATCATACA TAAGTCATTT AGTAACAGCC
5051  TTTGTGAAAT GAACTTGTTT ACTATTGGAG ATAACCACAC TTAATAAAGA
5101  AGAGACAGTG AAAGTACCAT CATAATTAAC CTAAATTTTT GTTATAGCAG
5151  AGTTTCTTGT TTAAAAAAAA ATAAAATCAT CTGAAAAGCA AAAATACAGT
5201  AAAATGTATA ATGAAGCTTT GCCAACCAGA CTGTGCTAGC AACAAATTTT
5251  TTTAAATAAG CTTTATGCAG TGGTAATAAG GTGGCCTCAA ATATATTGTG
5301       TCTGATGGAG AGTTATTAGT GAAATGAATG T   (SEQ. ID NO. 6)
```

Figure 8

```
   1 MAPPGCPGSC PNFAVVCSFL ERYGPLLDLP ELPFPELERV LQAPPPDVGN
  51 GEVPKELVEL HLKLMRKIGK SVTADRWEKY LIKYLCECQF DDNLKFKNII
 101 NEEDADTMRL QPIGRDKDGL MYWYQLDQDH NVRMYIEEQD DQDGSSWKCI
 151 VRNRNELAET LALLKAQIDP VLLKNSSQQD NSSRESPSLE DEETKKEEET
 201 PKQEEQKESE KMKSEEQPMD LENRSTANVL EETTVKKEKE DEKELVKLPV
 251 IVKLEKPLPE NEEKKIIKEE SDSFKENVKP IKVEVKECRA DPKDTKSSME
 301 KPVAQEPERI EFGGNIKSSH EITEKSTEET EKLKNDQQAK IPLKKREIKL
 351 SDDFDSPVKG PLCKSVTPTK EFLKDEIKQE EETCKRISTI TALGHEGKQL
 401 VNGEVSDERV APNFKTEPIE TKFYETKEES YSPSKDRNII TEGNGTESLN
 451 SVITSMKTGE LEKETAPLRK DADSSISVLE IHSQKAQIEE PDPPEMETSL
 501 DSSEMAKDLS SKTALSSTES CTMKGEEKSP KTKKDKRPPI LECLEKLEKS
 551 KKTFLDKDAQ RLSPIPEEVP KSTLESEKPG SPEAAETSPP SNIIDHCEKL
 601 ASEKEVVECQ STSTVGGQSV KKVDLETLKE DSEFTKVEMD NLDNAQTSGI
 651 EEPSETKGSM QKSKFKYKLV PEEETTASEN TEITSERQKE GIKLTIRISS
 701 RKKKPDSPPK VLEPENKQEK TEKEEEKTNV GRTLRRSPRI SRPTAKVAEI
 751 RDQKADKKRG EGEDEVEEES TALQKTDKKE ILKKSEKDTN SKVSKVKPKG
 801 KVRWTGSRTR GRWKYSSNDE SEGSGSEKSS AASEEEEEKE SEEAILADDD
 851 EPCKKCGLPN HPELILLCDS CDSGYHTACL RPPLMIIPDG EWFCPPCQHK
 901 LLCEKLEEQL QDLDVALKKK ERAERRKERL VYVGISIENI IPPQEPDFSE
 951 DQEEKKKDSK KSKANLLERR STRTRKCISY RFDEFDEAID EAIEDDIKEA
1001 DGGGVGRGKD ISTITGHRGK DISTILDEER KENKRPQRAA AARRKKRRRL
1051 NDLDSDSNLD EEESEDEPKI SDGSQDEFVV SDENPDESEE DPPSNDDSDT
1101 DFCSRRLRRH PSRPMRQSRR LRRKTPKKKY SDDDEEEESE ENSRDSESDF
1151 SDDFSDDFVE TRRRRSRRNQ KRQINYKEDS ESDGSQKSLR RGKEIRRVHK
1201 RRLSSSESEE SYLSKNSEDD ELAKESKRSV RKRGRSTDEY SEADEEEEEE
1251 EGKPSRKRLH RIETDEEESC DNAHGDANQP ARDSQPRVLP SEQESTKKPY
1301 RIESDEEEDF ENVGKVGSPL DYSLVDLPST NGQSPGKAIE NLIGKPTEKS
1351 QTPKDNSTAS ASLASNGTSG GQEAGAPEEE EDELLRVTDL VDYVCNSEQL
```

(SEQ. ID NO. 7)

Figure 9

852  EP_C_KK_C_GLPN  HPELILL_C_DS  _C_DSG_YH_TA_C_L  RPPLMIIPDG  EWF_C_PP (SEQ. ID NO. 8)

Figure 10A

```
   1 CGGCAGGGCA GCGGGGCGAT GAGGTGAGGA CGCCCGGGAA CCGGAGGCGG
  51 CACCGCGCGG CGCACGGACC TGGGACGCGG AGTCCTGAAG CCGGCGGACG
 101 GTTTTCGTAC GGGCGGCCGT GCGCGAGGCG AGGAGAGAAC ATTGAAAGTA
 151 TTCTCTAAGC TATTTGAAGA GAGTGACTAA ATGCACCTGG GTCAGGCTGT
 201 CTGTGGGTAT GAAGTGGTTG GGAGAATCCA AGAACATGGT GGTGAATGGC
 251 AGGAGAAATG GAGGCAAGTT GTCTAATGAC CATCAGCAGA ATCAATCAAA
 301 ATTACAGCAC ACGGGAAGG ACACCCTGAA GGCTGGCAAA AATGCAGTCG
 351 AGAGGAGGTC GAACAGATGT AATGGTAACT CGGGATTTGA AGGACAGAGT
 401 CGCTATGTAC CATCCTCTGG AATGTCCGCC AAGGAACTCT GTGAAAATGA
 451 TGACCTAGCA ACCAGTTTGG TTCTTGATCC CTATTTAGGT TTTCAAACAC
 501 ACAAAATGAA TACTAGCGCC TTTCCTTCGA GGAGCTCAAG GCATTTTTCA
 551 AAATCTGACA GTTTTTCTCA CAACAACCCT GTGAGATTTA GGCCTATTAA
 601 AGGAAGGCAG GAAGAACTAA AGGAAGTAAT TGAACGTTTT AAGAAAGATG
 651 AACACTTGGA GAAAGCCTTC AAATGTTTGA CTTCAGGCGA ATGGGCACGG
 701 CACTATTTTC TCAACAAGAA TAAAATGCAG GAGAAATTAT TCAAAGAACA
 751 TGTATTTATT TATTTGCGAA TGTTTGCAAC TGACAGTGGA TTTGAAATAT
 801 TGCCATGTAA TAGATACTCA TCAGAACAAA ATGGAGCCAA AATAGTTGCA
 851 ACAAAAGAGT GGAAACGAAA TGACAAAATA GAATTACTGG TGGGTTGTAT
 901 TGCCGAACTT TCAGAAATTG AGGAGAACAT GCTACTTAGA CATGGAGAAA
 951 ACGACTTCAG TGTCATGTAC TCCACAAGGA AAAACTGTGC TCAACTCTGG
1001 CTGGGTCCTG CTGCGTTTAT AAACCATGAT TGCAGACCTA ATTGTAAGTT
1051 TGTGTCAACT GGTCGAGATA CAGCATGTGT GAAGGCTCTA AGAGACATTG
1101 AACCTGGAGA AGAAATTTCT TGTTATTATG GAGATGGGTT CTTTGGAGAA
1151 AATAATGAGT TCTGCGAGTG TTACACTTGC GAAAGACGGG GCACTGGTGC
1201 TTTTAAATCC AGAGTGGGAC TGCCTGCGCC TGCTCCTGTT ATCAATAGCA
1251 AATATGGACT CAGAGAAACA GATAAACGTT TAAATAGGCT TAAAAAGTTA
1301 GGTGACAGCA GCAAAAATTC AGACAGTCAA TCTGTCAGCT CTAACACTGA
1351 TGCAGATACC ACTCAGGAAA AAAACAATGC AACTTCTAAC CGAAAATCTT
```

Figure 10B

```
1401  CAGTTGGCGT AAAAAAGAAT AGCAAGAGCA GAACGTTAAC GAGGCAATCT
1451  ATGTCAAGAA TTCCAGCTTC TTCCAACTCT ACCTCATCTA AGCTAACTCA
1501  TATAAATAAT TCCAGGGTAC CAAAGAAACT GAAGAAGCCT GCAAAGCCTT
1551  TACTTTCAAA GATAAAATTG AGAAATCATT GCAAGCGGCT GGAGCAAAAG
1601  AATGCTTCAA GAAAACTCGA AATGGGAAAC TTAGTACTGA AAGAGCCTAA
1651  AGTAGTTCTG TATAAAAATT TGCCCATTAA AAAAGATAAG GAGCCAGAGG
1701  GACCAGCCCA AGCCGCAGTT GCCAGCGGGT GCTTGACTAG ACACGCGGCG
1751  AGAGAACACA GACAGAATCC TGTGAGAGGT GCTCATTCGC AGGGGAGAG
1801  CTCGCCCTGC ACCTACATAA CTCGGCGGTC AGTGAGGACA AGAACAAATC
1851  TGAAGGAGGC CTCTGACATC AAGCTTGAAC CAAATACGTT GAATGGCTAT
1901  AAAAGCAGTG TGACGGAACC TTGCCCCGAC AGTGGTGAAC AGCTGCAGCC
1951  AGCTCCTGTG CTGCAGGAGG AAGAACTGGC TCATGAGACT GCACAAAAAG
2001  GGGAGGCAAA GTGTCATAAG AGTGACACAG GCATGTCCAA AAAGAAGTCA
2051  CGACAAGGAA AACTTGTGAA ACAGTTTGCA AAAATAGAGG AATCTACTCC
2101  AGTGCACGAT TCTCCTGGAA AAGACGACGC GGTACCAGAT TTGATGGGTC
2151  CCCATTCTGA CCAGGGTGAG CACAGTGGCA CTGTGGGCGT GCCTGTGAGC
2201  TACACAGACT GTGCTCCTTC ACCCGTCGGT TGTTCAGTTG TGACATCAGA
2251  TAGCTTCAAA ACAAAGACA GCTTTAGAAC TGCAAAAAGT AAAAAGAAGA
2301  GGCGAATCAC AAGGTATGAT GCACAGTTAA TCCTAGAAAA TAACTCTGGG
2351  ATTCCAAAT TGACTCTTCG TAGGCGTCAT GATAGCAGCA GCAAAACAAA
2401  TGACCAAGAG AATGATGGAA TGAACTCTTC CAAAATAAGC ATCAAGTTAA
2451  GCAAAGACCA TGACAACGAT AACAATCTCT ATGTAGCAAA GCTTAATAAT
2501  GGATTTAACT CAGGATCAGG CAGTAGTTCT ACAAAATTAA AAATCCAGCT
2551  AAAACGAGAT GAGGAAAATA GGGGGTCTTA TACAGAGGGG CTTCATGAAA
2601  ATGGGGTGTG CTGCAGTGAT CCTCTTTCTC TCTTGGAGTC TCGAATGGAG
2651  GTGGATGACT ATAGTCAGTA TGAGGAAGAA AGTACAGATG ATTCCTCCTC
2701  TTCTGAGGGC GATGAAGAGG AGGATGACTA TGATGATGAC TTTGAAGACG
2751  ATTTTATTCC TCTTCCTCCA GCTAAGCGCT TGAGGTTAAT AGTTGGAAAA
2801  GACTCTATAG ATATTGACAT TTCTTCAAGG AGAAGAGAAG ATCAGTCTTT
2851  AAGGCTTAAT GCCTAAGCTC TTGGTCTTAA CTTGACCTGG GATAACTACT
```

Figure 10C

```
2901  TTAAAGAAAT AAAAAATTCC AGTCAATTAT TCCTCAACTG AAAGTTTAGT
2951  GGCAGCACTT CTATTGTCCC TTCACTTATC AGCATACTAT TGTAGAAAGT
3001  GTACAGCATA CTGACTCAAT TCTTAAGTCT GATTTGTGCA AATTTTTATC
3051  GTACTTTTTA AATAGCCTTC TTACGTGCAA TTCTGAGTTA GAGGTAAAGC
3101  CCTGTTGTAA AATAAAGGCT CAAGCAAAAT TGTACAGTGA TAGCAACTTT
3151  CCACACAGGA CGTTGAAAAC AGTAATGTGG CTACACAGTT TTTTTAACTG
3201  TAAGAGCATC AGCTGGCTCT TTAATATATG ACTAAACAAT AATTTAAAAC
3251  AAATCATAGT AGCAGCATAT TAAGGGTTTC TAGTATGCTA ATATCACCAG
3301  CAATGATCTT TGGCTTTTTG ATTTATTTGC TAGATGTTTC CCCCTTGGAG
3351  TTTTGTCAGT TTCACACTGT TTGCTGGCCC AGGTGTACTG TTTGTGGCCT
3401  TTGTTAATAT CGCAAACCAT TGGTTGGGAG TCAGATTGGT TTCTTAAAAA
3451  AAAAAAAAAA ATGACATACG TGACAGCTCA CTTTTCAGTT CATTATATGT

3501  ACGAGGGTAG CAGTGTGTGG GATGAGGTTC GATACAGCGT ATTTATTGCT
3551  TGTCATGTAA ATTAAAAACC TTGTATTTAA CTCTTTTCAA TCCTTTTAGA
3601  TAAAATTGTT CTTTGCAAGA ATGATTGGTG CTTATTTTTT CAAAAATTTG
3651  CTGTGAACAA CGTGATGACA ACAAGCAACA TTTATCTAAT GAACTACAGC
3701  TATCTTAATT TGGTTCTTCA AGTTTTCTGT TGCACTTGTA AAATGCTACA
3751  AGGAATATTA AAAAAATCTA TTCACTTTAA CTTATAATAG TTTATGAAAT
3801  AAAAACATGA GTCACAGCTT TTGTTCTGTG GTAACCTATA AAAAAAGTTT
3851  GTCTTTGAGA TTCAATGTAA AGAACTGAAA ACAATGTATA TGTTGTAAAT
3901  ATTTGTGTGT TGTGAGACAT TTTTGTCATA AGAAATTAAA AGAACTTACC
3951  AGGAAGGTTT TTAAGTTTAG AAATATTCAT GCCAATAAAA TAGGAAATTA
4001  TAAATATATA GTTTTAAGCA CTGCATCAGT GGGAGTTCTT GGCTTATGTT
4051  AGTTTATGTT AGTTTATTAT GAAAACATCA AAGATTTTTT TGACTATATT
4101  ATCAGTTAAA CAAAAGGAG TCAGATTTAA TTTGTTTTTT GAAGCACTTT
4151  GAGAAATTAA TTTTAATTAA CTTAATGAGC AAATTTTTAT TACTACTTTA
4201  TGTTCAATAC CAGGTTCTTT TCATTTCTCT GGATTATTTT GCAAATCATT
4251  GGACAGAGAA TTTGGGAATA TAAATCTGTA ACAGGTGTTG ACACCAGTAG
4301  GTCTCTTTAT TTCTGGGAAA TGTGTACCTG TACTTTCTGA TATACAGTGT
```

Figure 10D

```
4351  TCCTAAGTAA AAATCAATTC AGGGGATTTG TATAGTGTCT ATAGGAAAGT
4401  AGCCCATGTC TTGAAATATG AAAAGGAATC TGAAGGTCAT GAAAAGTCCA
4451  GTGGAGAAAA TCTCAATGCT TACTGTTACT ACTAATTGAT TCCTACTAGT
4501  TTCCAGGTTT GGGGGGATAT TGTTTCAATG ACGCTCCTTA AGACTGTTGA
4551  TTGCCCATAG GTTCCAAATA GAAATTAAGA CTCATGAACA TTTTTAGAAA
4601  GTAGATTGTT TTCTCCTGGT TCTCTAAGGA ACTACTTCTG CAGTCTTACA
4651  TAGTCTCATC CTTGTTTGTT GTGGTGCAGT CGAACTCCTC AGGCGTTTGG
4701  AAAGCATGTG GTAGACCTTC TTCCACACCC ACCCATACCC CCGTTCACTG
4751  CGTCTGGAGG TCTTCAACAG TGAAGTAGGG CAGCCCACAC AGCCTCTCAG
4801  GAGCACCTGT CCGAGGCACC CGGAGCACTT TGCAGAGCAC GTCCAGCCCT
4851  CATGGGGTCC CTGCATAGAA ATGTGAACCC CTGCCACTGA GGAAGATGAA
4901  GGTAGACCCT GTGTCTGGAG GTGCTGGAGG GCAGCGGGTC ACCTCTTGTA
4951  TTCCCACCTT AGTTTGGGGT GTTTGAAGA GGTTCAGAGA CTAAATCTTA
5001  AACCTTATTT GAATACCAAC GATAGCTATT TTGGGAATTT CGATCTTAAA
5051  AAGTGACAAA ACACATTTCC CATTTTCATT TTTCAGCTGA ATTTTAGTAA
5101  CTTATTTTTG ATGTTTTAAT TTTATCATGG CCTCCTCTTT GGAGGCCAAC
5151  CTTCCCATGG GTCTCAAAGC AGTGACATTT GGTAGTAAAT CACTGCCTCT
5201  CAGGAGTCGG TATGCACAAG CACTCAGCAG CCACTGTTGA TGCCTTCTAG
5251  GGAAACCTAA TTTCCGTTGG TAAAGGTAGG GGCCTCGGAA CTGTTCCGGA
5301  TCTGCTGTAG AACTTCACCG TGTGGAATGG TGACAGCCAC ACACCGTTGA
5351  CCAGTTTAGA AGAGGTTGCA TTCAATAAAA CTCTTAGCTT GAGCTTATGC
5401  AATGATTGGT TAAGATTTTG GCATTGTAAG AATTAGGAGA TGATCATAGA
5451  AATATATGTA AAGTATTCAA TTTTCAATCA TTTTCAAATT ACTGTTATAA
5501  ATTGTTTTTG CTGAGTTGTA ATACTTTTGA GATACAATGT ATTCCTTGTA
5551  CTGAAAGAAT GAAAAAGGAC TTTTTCAGCA TTTGAGGTAA GTTCTTTAAC
5601  GTTTCATTAA AAACATTTTT TACAAATATT TTGTACATGC ACTTGCAGTA
5651  TTGAGGTTAA TCATTTTAAT AAATTCGGAA ATTAAAAAAA
```

(SEQ. ID NO. 9)

Figure 11

```
  1  MVVNGRRNGG KLSNDHQQNQ SKLQHTGKDT LKAGKNAVER RSNRCNGNSG
 51  FEGQSRYVPS SGMSAKELCE NDDLATSLVL DPYLGFQTHK MNTSAFPSRS
101  SRHFSKSDSF SHNNPVRFRP IKGRQEELKE VIERFKKDEH LEKAFKCLTS
151  GEWARHYFLN KNKMQEKLFK EHVFIYLRMF ATDSGFEILP CNRYSSEQNG
201  AKIVATKEWK RNDKIELLVG CIAELSEIEE NMLLRHGEND FSVMYSTRKN
251  CAQLWLGPAA FINHDCRPNC KFVSTGRDTA CVKALRDIEP GEEISCYYGD
301  GFFGENNEPC ECYTCERRGT GAFKSRVGLP APAPVINSKY GLRETDKRLN
351  RLKKLGDSSK NSDSQSVSSN TDADTTQEKN NATSNRKSSV GVKKNSKSRT
401  LTRQSMSRIP ASSNSTSSKL THINNSRVPK KLKKPAKPLL SKIKLRNHCK
451  RLEQKNASRK LEMGNLVLKE PKVVLYKNLP IKKDKEPEGP AQAAVASGCL
501  TRHAAREHRQ NPVRGAHSQG ESSPCTYITR RSVRTRTNLK EASDIKLEPN
551  TLNGYKSSVT EPCPDSGEQL QPAPVLQEEE LAHETAQKGE AKCHKSDTGM
601  SKKKSRQGKL VKQFAKIEES TPVHDSPGKD DAVPDLMGPH SDQGEHSGTV
651  GVPVSYTDCA PSPVGCSVVT SDSFKTKDSF RTAKSKKKRR ITRYDAQLIL
701  ENNSGIPKLT LRRRHDSSSK TNDQENDGMN SSKISIKLSK DHDNDNNLYV
751  AKLNNGPNSG SGSSSTKLKI QLKRDEENRG SYTEGLHENG VCCSDPLSLL
801  ESRMEVDDYS QYEEESTDDS SSSEGDEEED DYDDDFEDDF IPLPPAKRLR
851  LIVGKDSIDI DISSRRREDQ SLRLNA*     (SEQ. ID NO. 10)
```

APOPTIN-ASSOCIATING PROTEIN

PRIORITY CLAIM

This application claims priority under 35 U.S.C. §119 of European Patent applications EP 00250118.7, filed on Apr. 7, 2000 and EP 00200169.1, filed on Jan. 17, 2000, the contents of both of which are incorporated by this reference including all figures, claims and sequences identified therein.

BACKGROUND OF THE INVENTION

The invention relates to the field of apoptosis. Apoptosis is an active and programmed physiological process for eliminating superfluous, altered or malignant cells (Earnshaw, 1995; Duke et al., 1996). Apoptosis is characterized by shrinkage of cells, segmentation of the nucleus, condensation and cleavage of DNA into domain-sized fragments in most cells followed by internucleosomal degradation. The apoptotic cells fragment into membrane-enclosed apoptotic bodies. Finally, neighboring cells and/or macrophages will rapidly phagocytose these dying cells (Wylie et al., 1980; White, 1996). Cells grown under tissue-culture conditions and cells from tissue material can be analyzed for being apoptotic with agents staining DNA, for example, DAPI, which stains normal DNA strongly and regularly, whereas apoptotic DNA is stained weakly and/or irregularly (Noteborn et al., 1994; Telford et al., 1992).

The apoptotic process can be initiated by a variety of regulatory stimuli (Wyllie, 1995; White, 1996; Levine, 1997). Changes in the cell survival rate play an important role in human pathogenesis of diseases, for example, in cancer development and autoimmune diseases, where enhanced proliferation or decreased cell death (Kerr et al., 1994; Paulovich, 1997) is observed. A variety of chemotherapeutic compounds and radiation have been demonstrated to induce apoptosis in tumor cells, in many instances via wild-type p53 protein (Thompson, 1995; Bellamy et al., 1995; Steller, 1995; McDonell et al., 1995).

Many tumors, however, acquire a mutation in p53 during their development, often correlating with poor response to cancer therapy. Certain transforming genes of tumorigenic DNA viruses can inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-abl is associated with a strong resistance to various apoptosis-inducing chemotherapeutic agents (Hockenberry 1994; Sachs and Lotem, 1997).

For such tumors lacking functional p53 (representing more than half of the tumors), alternative antitumor therapies are under development based on induction of apoptosis independent of p53 (Thompson 1995; Paulovich et al., 1997). One has to search for the factors involved in induction of apoptosis, which do not need p53 and/or can not be blocked by antiapoptotic activities, such as Bcl-2 or Bcr-abl-like ones. These factors might be part of a distinct apoptosis pathway or might be (far) downstream of the apoptosis inhibiting compounds.

Apoptin is a small protein derived from chicken anemia virus (CAV; Noteborn and De Boer, 1995; Noteborn et al., 1991; Noteborn et al., 1994, 1998a) which can induce apoptosis in human malignant and transformed cell lines, but not in untransformed human cell cultures. In vitro, Apoptin fails to induce programmed cell death in normal lymphoid, dermal, epidermal, endothelial and smooth-muscle cells. However, when normal cells are transformed they become susceptible to apoptosis by Apoptin. Long-term expression of Apoptin in normal human fibroblasts revealed that Apoptin has no toxic or transforming activity in these cells (Danen-van Oorschot, 1997 and Noteborn, 1996).

In normal cells, Apoptin was found predominantly in the cytoplasm, whereas in transformed or malignant cells, i.e., characterized by hyperplasia, metaplasia or dysplasia, it was located in the nucleus, suggesting that the localization of Apoptin is related to its activity (Danen-van Oorschot et al. 1997).

Apoptin-induced apoptosis occurs in the absence of functional p53 (Zhuang et al., 1995a) and cannot be blocked by Bcl-2, Bcr-abl (Zhuang et al., 1995), or the Bcl-2-associating protein BAG-1 (Danen-Van Oorscho, 1997a; Noteborn, 1996).

Therefore, Apoptin is a therapeutic compound for the selective destruction of tumor cells or other hyperplasia, metaplasia or dysplasia, especially for those tumor cells which have become resistant to (chemo)-therapeutic induction of apoptosis due to the lack of functional p53 and (over)-expression of Bcl-2 and other apoptosis-inhibiting agents (Noteborn and Pietersen, 1998). It appears, that even premalignant, minimally transformed cells are sensitive to the death-inducing effect of Apoptin In addition, Noteborn and Zhang (1998) have shown that Apoptin-induced apoptosis can be used to diagnose cancer-prone cells and to treat cancer-prone cells.

The fact that Apoptin does not induce apoptosis in normal human cells, at least not in vitro, shows that a toxic effect of Apoptin treatment in vivo will be very low. Noteborn and Pietersen (1998) and Pietersen et al. (1999) have provided evidence that adenovirus expressed Apoptin does not have an acute toxic effect in vivo. In addition, in nude nice it was shown that Apoptin has a strong antitumor activity.

However, to further enlarge the array of therapeutic anticancer or antiautoimmune disease compounds available in the art, additional therapeutic compounds are desired that are designed to work alone, sequentially to, or jointly with Apoptin, especially in those cases wherein p53 is (partly) nonfunctional.

DISCLOSURE OF THE INVENTION

The invention provides novel therapeutic possibilities, for example, novel combinatorial therapies or novel therapeutic compounds that can work alone, sequentially to, or jointly with Apoptin, especially in those cases wherein p53 is (partly) nonfunctional.

In a first embodiment, the invention provides an isolated or recombinant nucleic acid or functional equivalent or fragment thereof encoding an Apoptin-associating proteinaceous substance capable of providing apoptosis, alone or in combination with other apoptosis inducing substances, such as Apoptin. Proteinaceous substance is herein defined as a substance comprising a peptide, polypeptide or protein, optionally having been modified by, for example, glycosylation, myristilation, phosphorylation, the addition of lipids, by homologous or heterologous di- or multimerisation, or any other (posttranslational) modifications known in the art.

Apoptin-associating is herein defined as belonging to the cascade of substances specifically involved in the cascade of events found in the apoptosis pathway as inducable by Apoptin, preferably those substances that are specifically involved in the p53-independent apoptosis pathway.

In a preferred embodiment, the invention provides an isolated or recombinant nucleic acid or functional equivalent or fragment thereof encoding an Apoptin-associating proteinaceous substance capable of providing apoptosis derived from a cDNA library, preferably a vertebrate cDNA library, such as derivable from poultry, but more preferably a mammalian cDNA library, preferably wherein said cDNA library comprises human cDNA. An Apoptin-associating proteinaceous substance obtained by determining a vertebrate analogue (preferably human) of an Apoptin-associating proteinaceous substance derived from an invertebrate cDNA library is also included.

In another embodiment, the invention provides an isolated or recombinant nucleic acid or functional equivalent or fragment thereof encoding an Apoptin-associating proteinaceous substance capable of providing apoptosis capable of hybridizing to a nucleic acid molecule encoding an Apoptin-associating proteinaceous substance capable of providing apoptosis as shown in FIG. 1, 2, 5 and/or 7A–7D, in particular encoding a novel protein capable of providing apoptosis or functional equivalent or functional fragment thereof called Apoptin-associating protein 2 or 3, abbreviated herein also as AAP-2 or AAP-3. FIGS. 1 and 2 show an approximately 1100 and 900 bp fragment of the AAP-2 fragment as depicted in FIGS. 7A–7D. All 3 nucleotide sequences encode a protein with at least the capability of binding to Apoptin and providing apoptosis. Of course, an isolated or recombinant nucleic acid or functional equivalent or fragment thereof encoding an additional Apoptin-associating proteinaceous substance capable of associating with the AAP-2 or AAP-3 protein are herewith also provided, means and methods to arrive at such an additional protein located in the Apoptin cascade follow those of the detailed description given herein. Knowledge derived from studying the AAP-2 and/or AAP-3 clones is exploited to determine a functional pathway in which AAP-2 and/or AAP-3 is/are involved, thus allowing the design of a therapeutic means of intervening in such a pathway.

A functional equivalent or a functional fragment thereof is a derivative or a fragment having the same kind of activity possibly in different amounts. It is clear to a person skilled in the art that there are different ways of arriving at a functional equivalent or functional fragment. A functional equivalent can, for example, be a point mutant or a deletion mutant or a equivalent derived from another species. Another way to arrive at a functional equivalent is a molecular evolution of equivalents and/or fragments having the same kind of activity possibly in different amounts.

In particular, the invention provides an isolated or recombinant nucleic acid or functional equivalent or fragment thereof encoding an Apoptin-associating proteinaceous substance capable of providing apoptosis being at least 60% homologous, preferably at least 70%, more preferably at least 80%, even more preferably 90% and most preferably at least 95% homologous to a nucleic acid molecule, or to a functional equivalent or functional fragment thereof, encoding an Apoptin-associating proteinaceous substance as shown in FIG. 1, 2, 5 or 7A–7D.

Furthermore, the invention provides a vector comprising a nucleic acid according to the invention. Examples of such a vector are given in the detailed description given herein, such as vector pMT2SM-AAP-2 or -AAP-3, pMT2SM vector expressing Myc-tagged APP-2 or AAP-3 cDNA, a plasmid expressing an Apoptin-associating protein fragment, and so on. These and other vectors are, for example, useful in finding additional Apoptin-associating proteinaceous substances from the cascade, as defined above.

In yet another embodiment, the invention provides a vector comprising a nucleic acid according to the invention, said vector comprising a gene-delivery vehicle, making the invention very useful in gene therapy. By equipping a gene delivery vehicle with a nucleic acid according to the invention, and by targeting said vehicle to a cell or cells that have been over-proliferating and/or have shown decreased death rates, said gene delivery vehicle provides said cell or cells with the necessary means for apoptosis, providing far reaching therapeutic possibilities.

Furthermore, the invention provides a host cell comprising a nucleic acid or a vector according to the invention. Examples comprise transformed or transfected bacterial or yeast cells as described in the detailed description herein. Preferred is a host cell according to the invention which is a transformed eukaryotic cell such as a yeast cell or a vertebrate cell, such as mammalian or Cos cells transformed or transfected with a nucleic acid or vector according to the invention. Said cells are in general capable to express or produce a proteinaceous substance capable of providing apoptosis with the ability to associate with Apoptin.

The invention furthermore provides an isolated or recombinant Apoptin-associating proteinaceous substance capable of providing apoptosis. As, for example, shown herein in FIG. 4, expression of such Apoptin-associating proteinaceous substance in cells such as tumor cells or other over-proliferating cells, induces the apoptic process. It can do so alone or in the presence of other apoptosis inducing substances such as Apoptin and especially so independent of p53 showing that also in those cases where (functional) p53 is absent, apoptosis can be induced by a substance according to the invention. In particular, the invention provides a proteinaceous substance according to the invention encoded by a nucleic acid, for example, comprising at least a part of an amino acid sequence as shown in FIG. 4 or a functional equivalent or functional fragment thereof capable of providing apoptosis alone or in combination with other apoptosis inducing substances such as Apoptin.

The invention also provides an isolated or synthetic antibody specifically recognising a proteinaceous substance or functional equivalent or functional fragment thereof according to the invention. Examples of such an antibody are given in the detailed description continued herein. Such an antibody is, for example, obtainable by immunizing an experimental animal with an Apoptin-associating proteinaceous substance or an immunogenic fragment or equivalent thereof and harvesting polyclonal antibodies from said immunized animal (as shown herein in the detailed description) or obtainable by other methods known in the art such as by producing monoclonal antibodies or (single chain) antibodies or binding proteins expressed from recombinant nucleic acid derived from a nucleic acid library, for example, obtainable via phage display techniques.

With such an antibody, the invention also provides a proteinaceous substance specifically recognizable by such an antibody according to the invention, for example, obtainable via immunoprecipitation, Western Blotting, or other immunological techniques known in the art.

Furthermore, the invention provides use of a nucleic acid, vector, host cell, or proteinaceous substance according to the invention for the induction of tumor-specific apoptosis, as, for example, shown in FIG. 4. In particular, such use is provided wherein said apoptosis is 53-independent. In particular, such use is also provided further comprising use of a nucleic acid encoding Apoptin or a functional equivalent or fragment thereof or use of Apoptin or a functional equivalent or fragment thereof As can be seen from FIG. 4, combining these Apoptin-inducing substances increases the apoptosis percentage of treated tumor cells.

Such use as provided by the invention is particularly useful from a therapeutic viewpoint. The invention provides herewith a pharmaceutical composition comprising a nucleic acid, vector, host cell, or proteinaceous substance. In addition, such a pharmaceutical composition according to the invention is provided further comprising a nucleic acid encoding Apoptin or a functional equivalent or fragment thereof.

Such a pharmaceutical composition is in particular provided for the induction of apoptosis, for example, wherein said apoptosis is p53-independent, for the treatment of a disease where enhanced cell proliferation or decreased cell death is observed, as is in general the case when said disease comprises cancer or autoimmune disease. Herewith the invention provides a method for treating an individual carrying a disease where enhanced cell proliferation or decreased cell death is observed comprising treating said individual with a pharmaceutical composition. In particular, these compositions comprise a factor of an apoptosis pathway, which is specific for transformed cells. Therefore, these compositions are essential for new treatments, but also for diagnosis of diseases related with aberrances in the apoptotic process, such as cancer, cancer-proneness and autoimmune diseases.

Furthermore, the invention provides a diagnostic assay based on the tumor-specific nuclear localization behavior of AAP-2, such as its dominant nuclear localization in human tumor cells but not in normal healthy cells.

The invention also provides an isolated or recombinant nucleic acid as set forth in SEQ ID NO. 6 (FIGS. 7A–7D). An isolated or recombinant proteinaceous substance encoded by a nucleic acid as set forth in SEQ ID NO. 6 is also included.

The invention provides an isolated or recombinant proteinaceous substance comprising the amino acid sequence as set forth in SEQ ID NO. 7 (FIG. 8).

The invention also provides an isolated or recombinant proteinaceous substance comprising the amino acid sequence as set forth in SEQ ID NO. 8 (FIG. 9).

In a further embodiment, the invention provides an assay to identify a putative effector of the activity of the proteinaceous substance encoded by a nucleic acid as set forth in SEQ ID NO. 6 (FIGS. 7A–7D) comprising bringing in contact a proteinaceous substance comprising the amino acid sequence as set forth in SEQ ID NO. 8 (FIG. 9) with said effector and determining the binding of said effector. Examples of methods to arrive at such an effector are binding studies, where an AAP-2 peptide comprising the PHD-finger domain (SEQ ID NO. 8) (FIG. 9) is bound to a matrix and is tested whether test substances bind to the AAP-2 peptide, or by coimmunoprecipitation of an AAP-2 peptide comprising the PHD-finger domain with test substances using antibodies generated against the AAP-2 peptide comprising the PHD-finger domain. Test substances are, for example, small organic compounds derived, e.g., from a compound library or peptides or proteins derived, e.g., from a peptide library or from a natural source like a cell extract. The test substances are, for example, labeled for easier detection. The substances found to bind to the PHD-finger domain may either enhance or inhibit one or more effects of AAP-2. This is, for example, tested by measuring the apoptotic activity of AAP-2 as described above in the presence of said substances and by determining the nuclear localization of AAP-2 as described above in the presence of said substances. It is clear to a person skilled in the art that an assay to identify a putative effector of the activity of a proteinaceous substance encoded by a nucleic acid as set forth in SEQ ID NO. 6 can also be performed with a functional equivalent or a functional fragment of SEQ ID NO. 8 having the same kind of activity possibly in different amounts.

The invention will be explained in more detail in the following detailed description, which does not limit the invention.

BRIEF DESCRIPTION OF THE DRAWINGS

Description of the Figures

FIG. 1 shows the partial sequence of vector pMT2SM-AAP-2-I.

FIG. 2 shows the partial sequence of vector pMT2SM-AAP-2-II.

FIG. 3 shows the amino-acid sequence of the analyzed region of the Apoptin-associating clone AAP-2-II. In addition, the three C-terminal amino acids H-E-G (bold) of the multiple cloning site of pACT are given to illustrate that the AAP-2 amino acid sequence is in frame with the GAL4-activation domain. This feature proves that the AAP-2-II region is indeed synthesized in yeast cells.

FIG. 4 shows the apoptotic activity of AAP-2 protein and/or Apoptin in human osteosarcoma-derived Saos-2 cells. (−): no apoptotic activity; (+): apoptotic activity; (++): strong apoptotic activity; (+++): very strong apoptotic activity. In total three independent experiments have been carried out.

FIG. 5 shows the partial sequence of vector pMT2SM-AAP-3.

FIG. 6 shows the amino-acid sequence of the analyzed region of the Apoptin-associating clone AAP-3. In addition, the three C-terminal amino acids H-E-G (bold) of the multiple cloning site of pACT are given to illustrate that the AAP-3 amino acid sequence is in frame with the GAL4-activation domain. This feature proves that the AAP-3 region is indeed synthesized in yeast cells.

FIGS. 7A–7D show the nucleic acid sequence of AAP-2.

FIG. 8 shows the amino acid sequence deduced from the nucleic acid sequence of FIG. 7A–7D.

FIG. 9 shows the PHD-finger domain of the AAP-2 protein.

FIGS. 10A–10D show the nucleic acid sequence of AAP-4.

FIG. 11 shows the amino acid sequence deduced from the nucleic acid sequence of FIGS. 10A–10D.

DETAILED DESCRIPTION OF THE INVENTION

We have used the yeast-2 hybrid system (Durfee et al., 1993) to identify Apoptin-associating cellular compounds, which are essential in the induction of apoptosis. The used system is an in vivo strategy to identify human proteins capable of physically associating with Apoptin. It has been used to screen cDNA libraries for clones encoding proteins capable of binding to a protein of interest (Fields and Song, 1989; Yang et al., 1992). The invention provides a, for example, novel Apoptin-associating protein, which is named Apoptin-associating protein 2 abbreviated as AAP-2. The invention also provides a method for inducing apoptosis through interference with the function of this newly discovered AAP-2 protein or functional equivalents or fragments thereof and/or the induction of apoptosis by means of (over)expression of AAP-2 or related gene or functional equivalents or fragments thereof. In addition, the invention also provides another Apoptin-associating protein, named AAP-3.

The invention also provides an antitumor therapy based on the interference with the function of AAP-2-like proteins and/or its (over)expression. An aberrant high level of AAP-2-like proteins will result in the induction of the opposite process of cell transformation, namely apoptosis. The invention furthermore provides a mediator of Apoptin-induced apoptosis, which is tumorspecific. The invention provides a therapy for cancer, autoimmune diseases or related diseases which is based on AAP-2-like proteins alone or in combination with Apoptin and/or Apoptin-like compounds.

Construction of pGBT9-VP3

For the construction of the bait plasmid, which enables the identification of Apoptin-associating proteins by means of a yeast-two-hybrid system, plasmid pET-16b-VP3 (Noteborn, unpublished results) was treated with NdeI and BamHI. The 0.4 kb NdeI-BamHI DNA fragment was isolated from low-melting-point agarose.

Plasmid pGBT9 (Clontech Laboratories, Inc., Palo Alto, USA) was treated with the restriction enzymes EcoRI and BamHI. The about 5.4-kb DNA fragment was isolated and ligated to an EcoRI-NdeI linker and the 0.4-kb DNA fragment containing the Apoptin-encoding sequences starting from its own ATG-initiation codon. The final construct containing a fusion gene of the GAL4-binding domain sequence and Apoptin under the regulation of the yeast promoter ADH was called pGBT-VP3 and was proven to be correct by restriction-enzyme analysis and DNA-sequencing according to the Sanger method (1977).

All cloning steps were essentially carried out as described by Maniatis et al. (1992). The plasmid pGBT-VP3 was purified by centrifugation in a CsCl gradient and column chromatography in Sephacryl S500 (Pharmacia).

GAL4-activation Domain-tagged cDNA Library

The expression vector pACT, containing the cDNAs from Epstein-Barr-virus-transformed human B cells fused to the GAL4 transcriptional activation domain, was used for detecting Apoptin-associating proteins. The pACT c-DNA library is derived from the lambda-ACT cDNA library, as described by Durfee et al. 1993.

Bacterial and Yeast Strains

The *E. coli* strain JM109 was the transformation recipient for the plasmid pGBT9 and pGBT-VP3. The bacterial strain electromax/DH10B was used for the transformation needed for the recovery of the Apoptin-associating pACT-cDNAs and was obtained from GIBCO-BRL, USA.

The yeast strain Y190 was used for screening the cDNA library and all other transformations, which are part of the used yeast-two-hybrid system.

Media

For drug selections, Luria Broth (LB) plates for *E. coli* were supplemented with ampicillin (50 microgram per ml). Yeast YPD and SC media were prepared as described by Rose et al. (1990).

Transformation of Competent Yeast Strain Y190 with Plasmids pGBT-VP3 and pACT-cDNA and Screening for Beta-galactosidase Activity The yeast strain Y190 was made competent and transformed according to the methods described by Klebe et al. (1983). The yeast cells were first transformed with pGBT-VP3 and subsequently transformed with pACT-cDNA, and these transformed yeast cells were grown on histidine-minus plates, also lacking leucine and tryptophan.

Hybond-N filters were layed on yeast colonies, which were histidine-positive and allowed to wet completely. The filters were lifted and submerged in liquid nitrogen to permeabilize the yeast cells. The filters were thawed and layed with the colony side up on Whattman 3MM paper in a petridish with Z-buffer (Per liter: 16.1 gr $Na_2HPO_4.7H_2O$, 5.5 gr $NaH_2PO_4.H_2O$, 0.75 gr KCl and 0,246 gr $MgSO_4.7H_2O$, pH 7.0) containing 0.27% beta-mercapto-ethanol and 1 mg/ml X-gal. The filters were incubated for at least 15 minutes or over night.

Recovery of Plasmids from Yeast

Total DNA from yeast cells, which were histidine- and beta-galactosidase-positive, was prepared by using the glusulase-alkaline lysis method as described by Hoffman and Winston (1987) and used to transform Electromax/DH10B bacteria via electroporation using a Bio-Rad GenePulser according the manufacturer's specifications.

Transformants were plated on LB media containing the antibiotic agent ampicillin.

Isolation of Apoptin-associating pACT Clones

By means of colony-filter assay, the colonies were lysed and hybridized to a radioactive-labeled 17-mer oligomer, which is specific for pACT (see also section Sequence analysis). Plasmid DNA was isolated from the pACT-clones and by means of XhoI digestion analysed for the presence of a cDNA insert.

Sequence Analysis

The subclone containing the sequence encoding the Apoptin-associating protein was partially sequenced using dideoxy NTPs according to the Sanger-method, which was performed by Eurogentec, Seraing, Belgium The used sequencing primer was a pACT-specific 17-mer comprising the DNA-sequence 5'-TACCACTACAATGGATG-3' (SEQ ID NO. 11).

The sequences of the Apoptin-associating cDNAs were compared with known gene sequences from the EMBL/Genbank.

Generation and Testing of Antibodies

In order to generate polyclonal antisera against the AAP-2 and AAP-3 protein, we designed three peptides per protein. These peptides were for AAP-2:

1) EVPKSTLESEKPGSP  (SEQ. ID NO. 12)  (19–33)

2) ISSRKKKPDSPPKVL  (SEQ. ID NO. 13)  (149–163)

3) TGSRTRGRWKYSSND  (SEQ. ID NO. 14)  (256–270)

The peptides for AAP-3 were:

IYQRSGERPVTAGEE  (SEQ. ID NO. 15)  (23–37)

DEQVPDSIDAREIFD  (SEQ. ID NO. 16)  (38–52)

RSINDPEHPLTLEEL  (SEQ. ID NO. 17)  (55–69)

The numbers in parenthesis correspond respectively to the amino acid sequences of FIG. 3 (SEQ. ID NO. 3)and FIG. 6 (SEQ. ID NO. 5).

These peptides were synthesized at Eurogentec (Belgium) with the standard addition of a C-terminal or N-terminal cysteine residue and all subsequent antibody syntheses were also performed there. These peptides were coupled to Keyhole Limpet Hemocyanin (KLH) and injected as a cocktail into two separate specific pathogen free rabbits with an immunization schedule of one injection and three subsequent boosts. Blood samples were taken before and after immunization. The sera were tested in-house for specific reactivity to the peptide cocktail by ELISA. The titers from each rabbit were high (>200,000). Furthermore, for certain subsequent purposes, the AAP-2 and AAP-3 antibodies were immune-purified using peptide cocktail coupled to immobilized diaminodipropylamine agarose columns (Pierce) according to the manufacturer's protocol.

The best AAP-2 and AAP-3 antibody preparation of the two generated was selected for further use. We tested the efficacy of this antibody by transfecting 6 cm plates of subconfluent primate COS-7 and human $U_2OS$ cells using the calcium phosphate coprecipitation method with 5 μg of the AAP-2-myc or AAP-3-myc plasmid DNA construct and, as a control, untransfected cells. Two days post-transfection, cells were washed briefly in PBS, lysed in RIPA buffer (10 mM Tris 7.5, 150 mM NaCl, 0.1% SDS, 1.0% NP-49 and 1.0 % sodium deoxycholate), clarified by centrifugation, and the supernatant fractionated on SDS-denaturing polyacrylamide gel electrophoresis. Proteins were Western-transferred to PVDF membranes (Immobilon, Millipore) using standard methodology. Membranes were blocked in 5% nonfat dry milk in tris-buffered saline containing 0.1% Tween-20, then incubated in the unpurified AAP-2 or AAP-3 antisera at a concentration of 1:5000. After a brief wash, membranes were further incubated in HRP-conjugated goat-anti-rabbit Ig at a concentration of 1:2000. After a thorough series of wash steps, proteins were detected using enhanced chemiluminescence (Amersham) according to the manufacturer's protocol and exposed to x-ray film and developed using standard automated machinery.

In addition, we tested the purified AAP-2 and AAP-3 antibody using immunoprecipitation in a manner the same as above, except that after centrifugation, the supernatant was added to 10 ul of AAP-2 or AAP-3 antibody precoupled to protein-A-sepharose beads, incubated for 1 hour with tumbling, then washed before fractionation on SDS-PAGE gels and Western analysis. Detection in this case was performed with the anti-myc tag monoclonal antibody 9E10 (Evan et al. 1985).

Finally, the purified antibody was tested for utility in immunofluorescence by including glass coverslips in the above transfections. Coverslips were fixed with 4% paraformaldehyde, blocked with normal goat serum, incubated in AAP-2 or AAP-3 antibody diluted 1:5, washed, incubated in FITC-conjugated goat-anti-rabbit Ig, mounted and visualized under fluorescence microscopy.

Results and Discussion

Apoptin induces specifically apoptosis in transformed cells, such as cell lines derived from human tumors. To identify the essential compounds in this cell-transformation-specific and/or tumor-specific apoptosis pathway, a yeast genetic screen was carried out.

We have used a human cDNA library, which is based on the plasmid vector pACT containing the complete cDNA copies made from Epstein-Barr virus-transformed human B cells (Durfee et al., 1993).

Construction of a Bait Plasmid Expressing a Fusion Gene Product of GAL4-DNA-binding Domain and Apoptin To examine the existence of Apoptin-associating proteins in the human transformed/tumorigenic cDNA library, a so-called bait plasmid had to be constructed. To that end, the complete Apoptin-encoding region, flanked by about 40 basepairs downstream from the Apoptin gene, was cloned in the multiple cloning site of plasmid pGBT9.

The final construct, called pGBT-VP3, was analyzed by restriction-enzyme analysis and sequencing of the fusion area between Apoptin and the GAL4-DNA-binding domain.

A Gene(Fragment) Encoding an Apoptin-associating Protein is Determined by Transactivation of a GAL4-responsive Promoter in Yeast The Apoptin gene is fused to the GAL4-DNA-binding domain of plasmid pGBT-VP3, whereas all cDNAs derived from the transformed human B cells are fused to the GAL4-activation domain of plasmid pACT. If one of the proteinaceous substances encoded by said cDNAs binds to Apoptin, the GAL4-DNA-binding domain will be in the vicinity of the GAL4-activation domain resulting in the activation of the GAL4-responsive promoter, which regulates the reporter genes HIS3 and LacZ.

The yeast clones containing plasmid expressing Apoptin and a plasmid expressing an Apoptin-associating protein fragment can grow on a histidine-minus medium and will stain blue in a beta-galactosidase assay. Subsequently, the plasmid with the cDNA insert encoding the Apoptin-associating protein can be isolated and characterized.

Before we could do so, however, we have determined that transformation of yeast cells with pGBT-VP3 plasmid alone, or in combination with an empty pACT vector, did not result in the activation of the GAL4-responsive promoter.

Identification of Apoptin-associating Protein Encoded by cDNA Derived from a Human Transformed B Cell Line We have found two independent yeast colonies, which upon transformation with pGBT-VP3 and pACT-cDNA were able to grow on a histidine-minus medium (also lacking leucine and tryptophan) and stained blue in a beta-galactosidase assay. These results indicate that the observed yeast colonies contain, besides the bait plasmid pGBT-VP3, a pACT plasmid encoding a potential Apoptin-associating protein.

Plasmid DNA was isolated from the positive yeast colony, which was transformed in bacteria. By means of a filter-hybridization assay using a pACT-specific labeled DNA-probe, 2 independent clones containing pACT plasmid could be determined. Subsequently, pACT DNA was isolated and digested with restriction enzyme XhoI, which resulted in the presence of a 1.1-kbp (clone I) and a 1.3-kbp (clone II) cDNA insert, respectively. Finally, the pACT plasmids containing the two independent cDNA inserts were partially sequenced by using the Sanger method (Sanger et al., 1977).

Description of Apoptin-associating Proteins

The yeast genetic screen for Apoptin-associating proteins resulted in the detection of two cDNA clones comprising a single type of protein, namely a novel protein called Apoptin-associating protein 2, abbreviated as AAP-2.

The determined DNA sequence part of the AAP-2 cDNA clones AAP-2-I and AAP-2-II are shown in FIG. 1 (SEQ. ID NO. 1) and 2 (SEQ. ID NO. 2), respectively. The amino acid sequence, derived from the detected DNA sequence of clone AAP-2-II is given in FIG. 3 (SEQ. ID NO. 3). Below the experiments will be described for AAP-2-II, which will be referred as AAP-2.

Construction of an Expression Vector for the Identification of AAP-2 Protein in Mammalian Cells To study whether the cloned cDNA AAP-2 indeed encode (Apoptin-associating) a protein product, we have carried out the following experiments.

The DNA plasmid pMT2SM contains the adenovirus 5 major late promoter (MLP) and the SV40 ori enabling high levels of expression of foreign genes in transformed mammalian cells, such as SV-40-transformed Cos cells.

Furthermore, the pMT2SM vector contains a Myc-tag (amino acids: EQKLISEEDL) (SEQ. ID NO. 18) which is in frame with the foreign-gene product. This Myc-tag enables the recognition of, e.g., Apoptin-associating proteins by means of the Myc-tag-specific 9E10 antibody.

The pMT2SM vector expressing Myc-tagged AAP-2 cDNA was constructed as follows. The pACT-AAP-2 cDNA clone was digested with the restriction enzyme XhoI and the cDNA insert was isolated. The expression vector pMT2SM was digested with XhoI and treated with calf intestine alkaline phosphatase and ligated to the isolated AAP-2 cDNA inserts. By sequence analysis, the pMT2SM constructs containing the AAP-2 cDNA in the correct orientation was identified.

The synthesis of Myc-tagged AAP-2 protein was analyzed by transfection of Cos cells with plasmid pMT2SM-AAP-2. As negative control, Cos cells were mock-transfected. Two days after transfection, the cells were lysed and Western-blot analysis was carried out using the Myc-tag-specific antibody 9E10.

The Cos cells transfected with pMT2SM-AAP-2 were proven to synthesize a specific Myc-tagged AAP-2 product with the size of approximately 70 kDa As expected, the lysates of the mock-transfected Cos cells did not contain a protein product reacting with the Myc-tag-specific antibodies.

These results indicate that we have been able to isolate a cDNA that is able to produce a protein product with the ability to associate to the apoptosis-inducing protein Apoptin.

Coimmunoprecipitation of Myc-tagged AAP-2 Protein with Apoptin in a Transformed Mammalian Cell System Next, we have analyzed the association of Apoptin and the AAP-2 protein by means of coimmunoprecipitations using the Myc-tag-specific antibody 9E10. The 9E10 antibodies were shown not to bind directly to Apoptin, which enables the use of 9E10 for carrying out coimmunoprecipitations with (myc-tagged) Apoptin-associating proteins and Apoptin.

To that end, Cos cells were cotransfected with plasmid pCMV-VP3 encoding Apoptin and with plasmid pMT2SM-AAP-2. As a negative control, cells were transfected with pCMV-VP3 expressing Apoptin and a plasmid pcDNA3.1.LacZ-myc/His-LacZ encoding the myc-tagged betagalactosidase, which does not associate with Apoptin.

Two days after transfection, the cells were lysed in a buffer consisting of 50 mM Tris (7.5), 250 mM NaCl, 5 mM EDTA, 0.1% Triton x100, 1 mg/ml $Na_4P_2O_7$ and freshly added protease inhibitors such as PMSF, Trypsine-inhibitor, Leupeptine and $Na_3VO_4$. The specific proteins were immunoprecipitated as described by Noteborn et al. (1998) using the Myc-tag-specific antibodies 9E10 and analyzed by Western blotting.

Staining of the Western blot with 9E10 antibodies and 111.3 antibodies, which are specifically directed against myc-tag and Apoptin, respectively, showed that the "total" cell lysates contained the 16-kDa Apoptin product and the Myc-tagged AAP-2 protein. By means of a specific LacZ polyclonal antibody, the beta-galactosidase product could be visualized.

Immunoprecipitation of the Myc-tagged AAP-2 products was accompanied by the immunoprecipitation of Apoptin product of 16 kDa. In contrast, immunoprecipitation of myc-tagged betagalactosidase did not result in a detectable coprecipitation of the Apoptin protein. In addition, immunoprecipitation of the Apoptin protein, by means of a polyclonal antibody directed against the C-terminal part of Apoptin (Noteborn and Danen, unpublished results) was accompanied by the immunoprecipitation of the AAP-2 product of approximately 70-kDa, but not by beta-galactosidase protein.

In total, three independent immunoprecipitation experiments were carried out, which all showed the specific associating ability of Apoptin protein to the AAP-2 protein.

These results indicate that the novel determined AAP-2 protein is able to specifically associate with Apoptin not only in the yeast background, but also in a mammalian transformed cellular system.

Over-expression of the Novel AAP-2 Protein in Human Transformed Cells Induces the Apoptotic Process In addition, we have examined whether AAP-2 carries apoptotic activity. First, we have analyzed the cellular localization of the novel AAP-2 protein in human transformed cells. To that end, the human osteosarcoma-derived Saos-2 cells were transfected, as described by Danen-van Oorschot (1997), with plasmid pMT2SM-AAP-2 encoding the myc-tagged AAP-2 protein, respectively.

By indirect immunofluorescence using the myc-tag-specific antibody 9E10 and DAPI, which stains the nuclear DNA, it was shown that AAP-2 protein was mainly present in the nucleus of most of the tumor cells and in a minor part of the cells both in the nucleus and cytoplasm or cytoplasm alone. These features suggest that, at least in human tumor cells, AAP-2 is involved in nuclear transport processes.

Already, three days after transfection, a significant amount of Saos-2 cells synthesizing AAP-2 underwent induction of apoptosis. These AAP-2-positive cells were aberrantly stained with DAPI, which is indicative for induction of apoptosis (Telford, 1992, Danen-van Oorschot, 1997). Cells expressing Apoptin also underwent apoptosis, whereas as expected the cells synthesizing the nonapoptotic betagalactosidase (LacZ) protein did not. Coexpression of Apoptin and AAP-2 protein in human tumor cells, such as Saos-2 cells, results in a slightly faster apoptotic process than as with the expression of Apoptin or AAP-2 protein alone. The results are shown in FIG. 4.

The fact that AAP-2 protein can induce apoptosis in p53-minus Saos-2 cells indicates that AAP-2 can induce p53-independent apoptosis. These results imply that AAP-2 can be used as an antitumor agent in cases where other (chemo)therapeutic agents will fail. Furthermore, the finding that both Apoptin and AAP-2 induce a p53-independent pathway indicates that AAP-2 fits in the Apoptin-induced apoptotic pathway.

In conclusion, we have identified an Apoptin-associating protein, namely the novel AAP-2 protein, which is mainly present in the nucleus and able to induce (p53-independent) apoptosis in human tumor cells.

AAP-2 does not Induce Apoptosis in Human Normal Diploid Cells

Next, we have examined whether AAP-2 behaves similar in normal human diploid nontransformed cells as has been found for AAP-2 in human tumor cells.

To that end, human diploid VH10 fibroblasts (Danen-Van Oorschot, 1997) were transfected using Fugene according to the protocol of the supplier (Roche, Almere, The Netherlands) with plasmid pMT2SM-AAP-2b encoding the myc-tagged AAP protein. In parallel, human tumor-derived Saos-2 cells were also transfected with plasmid pMT2SM-AAP-2.

Three days after transfection, the cells were harvested and analyzed by indirect immunofluorescence using the myc-tag-specific antibody 9E10. Within the majority of AAP-2-positive human diploid cells, AAP-2 is located in the cytoplasm only or both in the nucleus and cytoplasm As expected, in most of the human tumor Saos-2 cells, AAP-2 is only located in the nucleus. Furthermore, the AAP-2-positive human normal diploid fibroblasts did not show a sign of AAP-2-induced apoptosis, as was examined by DAPI staining (see above).

In conclusion, we have identified an Apoptin-associating protein, namely AAP-2, which has a tumor-specific preference for induction of apoptosis and nuclear accumulation.

Further Sequence Analysis

A further sequence analysis of the human AAP-2 nucleic acid sequence yielded the 5331 bp long nucleic acid sequence given in FIGS. 7A–7D (SEQ. ID NO. 6). An open reading frame was found in this nucleic acid sequence at position 300–4499. The deduced amino acid sequence is given in FIG. 8 (SEQ. ID NO. 7).

A protein domain called PHD-finger was found in the amino acid sequence of the human AAP-2 protein. It spans the region of amino acid 852 to amino acid 900. The $Cys_4$-His-$Cys_3$ zinc-finger-like motif which is characteristic for a PHD-finger domain (R. Aasland et al., 1995; TIBS 20, 56–59) is found in said region (see, FIG. 9).

The PHD-finger is found in nuclear proteins thought to be involved in chromatin-mediated transcriptional regulation. The PHD-finger was originally identified in a set of proteins that includes members of the Drosophila Polycomb and trithorax group genes. These genes regulate the expression of the homeotic genes through a mechanism thought to involve some aspect of chromatin structure. Other proteins which have this motif also have additional domains or characteristics that support that suggestion that the PHD-finger is involved in chromatin-mediated gene regulation. PHD-fingers are thought to be protein-protein interaction domains. Such protein-protein interactions are important for, e.g., the activity of multicomponent complexes involved in transcriptional activation or repression. PHD-fingers may also recognize a family of related targets in the nucleus such as the nucleosomal histone tails (R. Aasland et al., 1995; TIBS 20, 56–59).

PHD-finger domains are also found in a number of proteins closely associated with human tumorigenisis such as HRX/ALL1/MLL/Htrx, CBP, MOZ, all of which are part of aberrant fusion proteins derived from chromosomal translocations found in a high percentage of human leukemias (for review see Jacobson and Pillus, 1999; Current Opinion in Genetics & Dev. 9, 175–184). Other PHD-finger domain-containing proteins are overexpressed in certain tumor types (Lu, P. J. et al, 1999; J.Biol. Chem. 274, 15633–45).

Therefore, interfering with the functional activity of the PHD-finger domain of AAP-2 should have therapeutic effects against human tumors. The PHD-finger domain can be used to identify substances which bind to the PHD-finger domain. This can be done by methods known to persons skilled in the art, e.g., by binding studies, where an AAP-2 peptide comprising the PHD-finger domain is bound to a matrix and it is tested whether test substances bind to the AAP-2 peptide or by coimmunoprecipitation of an AAP-2 peptide comprising the PHD-finger domain with test substances using antibodies generated against the AAP-2 peptide comprising the PHD-finger domain. Test substances may be small organic compounds derived, e.g., from a compound library or peptides or proteins derived, e.g., from a peptide library or from a natural source like a cell extract. The test substances may be labeled for easier detection. The substances found to bind to the PHD-finger domain may either enhance or inhibit one or more effects of AAP-2. This can be tested by measuring the apoptotic activity of AAP-2 as described above in the presence of said substances and by determining the nuclear localization of AAP-2 as described above in the presence of said substances.

Another Apoptin-associating Protein

The genetic yeast screen with pGBT-VP3 as bait plasmid and pACT plasmid containing cDNAs from transformed human B cells also delivered the novel gene Apoptin-associating protein 3 (AAP-3). The DNA sequence of the AAP-3 is shown in FIG. 5, whereas the AAP-3 cDNA-encoded amino-acid sequence is shown in FIG. 6.

To analyze into further detail the associating properties of Apoptin and this AAP-3 protein, we have expressed a Myc-tagged AAP-3 cDNA by means of the pSM2NT vector (as described for AAP-2) in transformed mammalian Cos cells. Western blot analysis using the Myc-tag-specific antibodies 9E10 showed a specific (Myc-tagged) AAP-3 protein of approximately 22-kDa. This major 22-kDa AAP-3 product is accompanied by smaller and larger minor AAP-3-specific products. These results indicate that the isolated cDNA indeed encodes a protein of the expected size.

Next, immunoprecipitation assays were carried out with transiently transfected Cos cells cosynthesizing Myc-tagged AAP-3 and Apoptin. The results clearly showed that both 9E10 antibodies and Apoptin-specific 111.3 antibodies precipitate AAP-3 protein and Apoptin, which indicates that Apoptin associates with this new AAP-3 protein in a mammalian transformed background. In total, three independent immunoprecipitation experiments were carried out, which all showed the associating ability of Apoptin to the AAP-3 protein.

Immunofluorescence assays of human transformed Saos-2 cells and normal diploid VH10 fibroblasts expressing AAP-3 revealed that AAP-3 is located in both cell types predominantly in the cytoplasm and nucleus, but in lower percentages also mainly in the nucleus or mainly in the cytoplasm. Cosynthesis of AAP-3 and Apoptin in both cell types showed a clear perinuclear colocalization of AAP-3 and Apoptin. Tumor cells that have become apoptotic showed a nuclear localization of Apoptin and a perinuclear stainings pattern of AAP-3. As expected, normal diploid VH10 cells synthesizing both Apoptin and AAP-3 did not undergo apoptosis.

These data indicate that AAP-3 will release Apoptin when the cell has become tumorigenic and/or transformed, resulting in the nuclear localization of Apoptin and induction of apoptosis.

In summary, our findings prove that our newly discovered AAP-3 protein is able to associate to the tumor-specific apoptosis-inducing protein Apoptin in both a yeast and mammalian cellular background. Therefore, this AAP-3 protein plays an important role in the induction of (Apoptin-regulated) tumors-specific apoptosis.

Utility of AAP-2 and AAP-3 Antisera

The best AAP-2 and AAP-3 antibody preparations obtained from the two rabbit derived antisera were selected for further use. We tested the efficacy of these antibody preparations against AAP-2 and AAP-3, respectively, by transfecting primate COS-7 and human $U_2OS$ cells with the AAP-2-myc or AAP-3-myc construct. Western analysis showed that the approximately 70 kDa AAP-2-myc protein and the approximately 22 kDa AAP-3-myc were detected strongly only in samples where the DNA was transfected. Similarly, in immunoprecipitation experiments, AAP-2-myc or AAP-3-myc protein was also strongly detected. Finally, localization of AAP-2-myc or AAP-3-myc protein in a cell using the AAP-2 or AAP-3 antibody could be determined by immunofluorescence analysis.

Overexpression of 2 Apoptin-associating Proteins

The genetic yeast screen with pGBT-VP3 as bait plasmid and pACT plasmid containing cDNAs from transformed human B cells also delivered another gene, which also encodes an Apoptin-associating protein. This Apoptin-associating protein was called AAP4 (see copending application EP00204396.6, which is incorporated herein by reference). The nucleic acid sequence of AAP-4 is shown in FIGS. 10A–10D (SEQ. ID NO. 9). An open reading frame was found in this nucleic acid sequence at position 236 to 2866. The deduced amino acid sequence is given in FIG. 11 (SEQ. ID NO. 10). Just like AAP-2 and AAP-3, AAP4 is able to associate with Apoptin not only in the yeast background, but also in a mammalian transformed cellular system. Furthermore, this protein is present in the nucleus and able to induce (p53-independent) apoptosis in human tumor cells. A functional equivalent or a functional fragment of AAP-4 is herein also included. A functional equivalent or a functional fragment of AAP-4 is a derivative or a fragment having the same kind of activity possibly in different amounts. It is clear to a person skilled in the art that there are different ways of arriving at a functional equivalent or functional fragment. A functional equivalent can, for example, be a point mutant or a deletion mutant or a equivalent derived from another species. Another way to arrive at a functional equivalent is a molecular evolution of equivalents and/or fragments having the same kind of activity possibly in different amounts.

To study whether two separate Apoptin-associating proteins can not only bind to Apoptin but also to another Apoptin-associating protein, we carried out the following experiment.

Immunoprecipitation assays were carried out with transiently transfected Cos cells cosynthesizing Myc-tagged AAP-3 and Myc-tagged AAP-4. The results clearly showed that antibodies directed against AAP-3 and antibodies directed against AAP-4 both precipitate AAP-3 and AAP-4, which suggests that AAP-3 and AAP-4 associate in this mammalian transformed background. In total, three independent immunoprecipitation experiments were carried out, which all showed the associating ability of AAP-3 and AAP-4.

The fact that two proteins, which showed to be Apoptin-associating proteins can independently coassociate in the absence of Apoptin strengthens the idea that the AAP-3/Apoptin coassociation is physiologically relevant.

Diagnostic Assay for Cancer Cells

Based on the present report, we can conclude that the cellular localization of AAP-2 is different in tumorigenic/transformed human cells in comparison to normal human nontransformed cells. Furthermore, accumulation of AAP-2 in the nucleus correlates with apoptosis induction, whereas cytoplasmic/nuclear localization correlates with cell viability and normal proliferative capacity. Therefore, we are able to develop a diagnostic assay for the identification of (human) cancer cells versus normal "healthy" nontransformed cells.

The assay consists of transfecting "suspicious" (human) cells, for instance from human origin, with a plasmid encoding AAP-2 or infecting the cells with viral vectors expressing AAP-2. Subsequently, the cells will be examined 1) for the ability to undergo apoptosis by the over-expressing AAP-2 gene and 2) for a main shift in the localization of AAP-2 from the cytoplasm to the nucleus.

The intracellular localization of AAP-2 can be determined, using an immunofluorescence assay with monoclonal antibodies specific for AAP-2 and/or specific for a tag linked to AAP-2 such as the herein described nyc-tag. If the percentage of apoptosis and/or the nuclear localization of AAP-2 in the analyzed cells expressing AAP-2 is significantly higher than in AAP-2-positive control "healthy" cells, one can conclude that the analyzed cells has become tumorgenic/transformed. As positive control known human tumorigenic cells will be used for expressing AAP-2.

Coexpression of SV40 Large T Antigen and AAP-2 Results in Translocation of AAP-2 and Induction of Apoptosis We have examined the effect of expression of transforming genes on AAP-2-induced apoptosis in normal human cells derived from healthy individuals. To that end, human VH10 diploid fibroblasts were transiently cotransfected with plasmid pMT2SM-AAP-2 encoding AAP-2 protein and either plasmid pR-s884 encoding SV40 large T antigen, or the negative-control plasmid pCMV-neo (Noteborn and Zhang, 1998).

By indirect immunofluorescence, the cells were analyzed for AAP-2-induced apoptosis. The normal VH10 cells did not undergo apoptosis when AAP-2 was transfected with the negative-control plasmid. The results showed, as expected, that expression of AAP-2 is not able to induce apoptosis in normal human diploid cells, confirming the above mentioned data. However, normal diploid human fibroblasts expressing both AAP-2 and SV40 large T antigen underwent AAP-2-induced apoptosis.

The transition of normal human cells, from AAP-2-resistance to AAP-2-susceptibility, can probably be explained by the fact that the AAP-2 protein translocates from a cytoplasmic localization to a nuclear localization. This transition becomes apparent already 2 days after transfection of plasmids encoding the transforming protein SV40 large T antigen. One can conclude that an event takes place, in this example due to expression of a transforming product derived from a DNA-tumor virus, which results in the translocation of over-expressed AAP-2 from the cytoplasm to the nucleus, which is followed by induction of apoptosis.

Diagnostic Assay for Cancer-inducing Genes, Agents and Cancer-proneness Based on AAP-2-Induced Apoptosis Based on the present report, we are able to develop a diagnostic assay for the identification of cancer-inducing and/or transforming agents or genes.

A first type of assay consists of transfecting "normal" cells, for instance from human origin, with a plasmid encoding AAP-2, or infecting the cells with viral vectors expressing AAP-2, together with a plasmid encoding a putative transforming/cancer-inducing gene. Subsequently, the cells will be examined 1) for the ability to undergo apoptosis by the over-expressing AAP-2 gene and 2) for a shift in the localization of AAP-2 from the cytoplasm to the nucleus.

The intracellular localization of AAP-2 can be determined using an immunofluorescence assay with monoclonal antibodies specific for AAP-2 and/or specific for a tag linked to AAP-2 such as the herein described myc-tag. If the percentage of apoptosis and/or the nuclear localization of AAP-2 in normal cells coexpressing AAP-2 and the putative transforming/cancer-inducing gene is significantly higher than in AAP-2-positive control cells expressing a control plasmid, one can conclude that the analyzed gene indeed has transforming/cancer-inducing activity.

A second example of a diagnostic test is based on the treatment of cultured normal diploid cells with a putative carcinogenic agent. The agent can be added, for instance, to the culture medium for various lengths of time. Subsequently, the cells are transfected with a plasmid encoding AAP-2. This approach can also be carried out by first transfecting/infecting the normal diploid cells and then treating the cells with the agent to be tested. The subsequent steps of the assay are the same as the first type of diagnostic assay described in this section. If the percentage of apoptosis and/or the nuclear localization of AAP-2 in normal cells expressing AAP-2 and the putative carcinogenic agent is significantly higher than in AAP-2-positive control cells expressing a control agent, one can conclude that the analyzed agent indeed has transforming/cancer-inducing activity.

A third example of a diagnostic test is based on the treatment of cultured normal diploid cells derived from a skin biopsy of the potential cancer-prone individual to be tested and cultured in suitable medium. Next, the cells are irradiated with UV and subsequently transfected with a plasmid encoding AAP-2 or infected with a viral vector expressing AAP-2 or the cells are first transfected and/or infected and then irradiated. In parallel, diploid cells from a normal healthy individual will be used as a control.

The subsequent steps of the assay are the same as the first type of diagnostic assay described in this section. If after UV-treatment the percentage of apoptosis and/or the nuclear localization of AAP-2 in diploid cells derived from the potential cancer-prone individual is significantly higher than in UV-treated AAP-2-positive control cells, one can conclude that the analyzed cells are cancer-proneness cells.

REFERENCES

1. Bellamy, C. O. C., Malcomson, R. D. G., Harrison, D. J., and Wyllie, H. 1995. Cell death and disease: The biology and regulation of apoptosis. Seminars in Cancer Biology 6, 3–12.
2. Danen-Van Oorschot, A. A. A. M., Fischer, D. F., Grimbergen, J. M., Klein, B., Zhuang, S.-M., Falkenburg, J. H. F., Backendorf, C., Quax, P. H. A., Van der Eb, J. A., and Noteborn, M. H. M. (1997). Apoptin induces apoptosis in human transformed and malignant cells but not in normal cells. Proceedings National Academy Sciences, USA: 94, 5843–5847.
3. Danen-Van Oorschot, A. A. A. M, Den Hollander, A., Takayama, S., Reed, J., Van der Eb, A. J. and Noteborn, M. H. M. (1997a). BAG-1 inhibits p53-induced but not Apoptin-induced apoptosis. Apoptosis 2, 395–402.
4. Duke, R. C., Ocjius, D. M., Young, J, D-E. (1996). Cell suicide in health and disease. Scientific American December 1996, 48–55.
5. Durfee, T., Becherer, K, Chen, P.-L., Yeh, S.-H., Yang, Y., Kilburn, A. E., Lee, W.-H., and Elledge, S. J. (1993). The retinoblastoma protein associates with the protein phosphate type I catalytic subunit. Genes and Development 7, 555–569.
6. Earnshaw, W. C., 1995. Nuclear changes in apoptosis. Current Opinion in Cell Biology 7, 337–343.
7. Fields, S. and Song, O. K. (1989). A novel genetic system to detect protein-protein interactions. Nature 340, 245–246.
8. Hockenberry, D. M. (1994). Bcl-2 in cancer, development and apoptosis. Journal of Cell Science, Supplement 18, 51–55.
9. Hoffman, C. S. and Winston, F. (1987). A ten-minute DNA preparation from yeast efficiently releases autonomous plasmids for transformation of *Escherichia coili*. Gene 57, 267–272.
10. Kerr, J. F. R., Winterford, C. M., and Harmon, B. V. (1994). Apoptosis: Its significance in cancer and cancer therapy. Cancer 73, 2013–2026.
11. Klebe, R. J., Harriss, J. V., Sharp, Z. D., and Douglas, M. G. (1983). A general method for polyethylene-glycol-induced genetic transformation of bacteria and yeast. Gene 25, 333–341.
12. Levine, A. J. (1997). p53, the cellular gatekeeper for growth and division. Cell 88, 323–331.
13. Maniatis, T., Fritsch, E. F., and Sambrook, J. (1982). Molecular Cloning: A Laboratory Manual. CSHL Press, New York, USA.
14. McDonell T. J., Meyn, R. E., Robertson, L. E. (1995). Implications of apoptotic cell death regulation in cancer therapy. Seminars in Cancer Biology 6, 53–60.
15. Noteborn, M. H. M. (1996). PCT application WO 96/41191. Apoptin induces apoptosis in human transformed and malignant cells but not in normal cells as essential characteristic for the development of an anti-tumor therapy.
16. Noteborn, M. H. M., and De Boer, G. F. (1996). Patent USA/no. 03/0, 335.
17. Noteborn, M. H. M., De Boer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131–3139.
18. Noteborn, M. H. M., and Pietersen, A. (1998). A gene delivery vehicle expressing the apoptosis-inducing proteins VP2 and/or Apoptin. PCT Application no. PCT/NL98/00213.
19. Noteborn, M. H. M., Todd, D., Verschueren, C. A. J., De Gauw, H. W. F. M., Curran, W. L., Veldkamp, S., Douglas, A. J., McNulty, M. S., Van der Eb, A. J., and Koch, G. (1994). A single chicken anemia virus protein induces apoptosis. Journal of Virology 68, 346–351.
20. Noteborn, M. H. M., Verschueren, C. A. J., Koch, G., and Van der Eb, A. J. (1998). Simultaneous expression of recombinant baculovirus-encoded chicken anemia virus (CAV) proteins VP 1 and VP2 is required for formation of the CAV-specific neutralizing epitope. Journal General Virology, 79, 3073–3077.
21. Noteborn, M. H. M., and Zhang, Y. (1998). Methods and means for determining the transforming capability of agents, for determining the predisposition of cells to become transformed and prophylactic treatment of cancer using Apoptin-like activity. PCT Application No. PCT/NL98/00457.
22. Noteborn, M. H. M., Danen-van Oorschot, A. A. A. M., Van der Eb, A. J. (1998a). Chicken anemia virus: Induction of apoptosis by a single protein of a single-stranded DNA virus. Seminars in Virology 8, 497–504.
23. Paulovich, A. G., Toczyski, D., Hartwell, H. (1997). When checkpoints fail Cell 88, 315–321.
24. Pietersen, A. M., Van der Eb, M. M., Rademaker, H. J., Van den Wollenberg, D. J. M., Rabelink, M. J. W. E., Kuppen, P. J. K., Van Dierendonck, J. H., Van Ormondt, H., Masman, D., Van de Velde, C. J. H., Van der Eb, Hoeben, R. C., and Noteborn, M. H. M. (1999). Specific tumor-cell killing with adenovirus vectors containing the Apoptin gene. Gene Therapy 6, 882–892.
25. Rose, M. D., Winston, F., and Hieter, P. (1990). Methods in yeast genetics. A laboratory course manual. Cold Spring Harbor Laboratory Press, Cold Spring Harbor, N.Y., USA.
26. Sachs, L. and Lotem, J. (1993). Control of programmed cell death in normal and leukemia cells: New implications for therapy. Blood 82, 15–21.
27. Sanger, F., Nicklen, S., and Coulsen, A. R. (1977). DNA sequencing with chain-terminating inhibitors. Proceedings National Academic Sciences USA 74, 5463–5467.
28. Steller, H. (1995). Mechanisms and genes of cellular suicide. Science 267, 1445–1449.
29. Telford, W. G., King, L. E., Fraker, P. J. (1992). Comparative evaluation of several DNA binding dyes in the detection of apoptosis-associated chromatin degradation by flow cytometry. Cytometry 13, 137–143.
30. Teodoro, J. G. and Branton, P. E. (1997). Regulation of apoptosis by viral gene products. Journal of Virology 71, 1739–1746.
31. Thompson, C. B. (1995). Apoptosis in the pathogenesis and treatment of disease. Science 267, 1456–1462.
32. White, E. (1996). Life, death, and the pursuit of apoptosis. Genes and development 10, 1–15.
33. Wyllie, A. H. (1995). The genetic regulation of apoptosis. Current Opinion in Genetics and Development 5, 97–104.
34. Wyllie, A. H., Kerr, J. F. R., Currie, A. R. (1980). Cell death: The significance of apoptosis. International Review of Cytology 68, 251–306.
35. Yang, X., Hubbard, E. J. A., and Carlson, M. (1992). A protein kinase substrate identified by the two-hybrid system. Science 257, 680–682.
36. Zhuang, S.-M., Landegent, J. E., Verschueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. Leukemia 9 S1, 118–120.
37. Zhuang, S.-M., Shvarts, A., Van Ormondt, H., Jochemsen, A-G., Van der Eb, A. J., Noteborn, M. H. M. (1995). Apoptin, a protein derived from chicken anemia virus, induces a p53-independent apoptosis in human osteosarcoma cells. Cancer Research 55, 486–489.
38. R. Aasland et al., 1995; TIBS 20, 56–59.
39. Jacobson and Pillus, 1999; Current Opinion in Genetics & Dev. 9, 175–184.
40. Lu, P. J. et al; 1999; J.Biol. Chem. 274, 15633–45.
41. Evan G. I., Lewis G. K, Ramsay G. Bishop J. M., (1985); Isolation of monoclonal antibodies specific for human c-myc proto-oncogene product. Mol. Cell. Biol. Dec 5 (12), 3610–3616;
42. Noteborn et al. (2000) European patent application 00204396.6, Apoptin-associating protein.

What is claimed is:

1. An isolated or recombinant nucleic acid encoding a protein capable of inducing apoptosis in vitro, encodes SEQ ID NO:3.

2. The isolated or recombinant nucleic acid of claim 1 wherein the isolated or recombinant nucleic acid is derived from a cDNA library.

3. The isolated or recombinant nucleic acid of claim 2 wherein said cDNA library comprises human cDNA.

4. A vector comprising the nucleic acid of claim 1.

5. A host cell comprising the nucleic acid of claim 1.

6. The host cell of claim 5 wherein said host cell is a eukaryotic cell.

7. A composition comprising the nucleic acid of claim 1.

8. The composition of claim 7 further comprising: a second nucleic acid encoding a protein capable of inducing apoptosis.

9. The composition of claim 8 wherein said nucleic acids are present in an amount sufficient to induce apoptosis.

10. The composition of claim 9 wherein said apoptosis is p53-independent.

* * * * *

UNITED STATES PATENT AND TRADEMARK OFFICE
CERTIFICATE OF CORRECTION

PATENT NO. : 6,809,189 B2
DATED : October 26, 2004
INVENTOR(S) : Mathieu Hubertus M. Noteborn et al.

It is certified that error appears in the above-identified patent and that said Letters Patent is hereby corrected as shown below:

Column 2,
Line 24, insert a period after "Apoptin".
Line 33, change "nice" to -- mice --.

Column 3,
Line 60, change "APP" to -- AAP --.

Column 4,
Line 65, insert a period after "thereof".

Column 8,
Line 38, insert a period after "Belgium".

Column 15,
Line 29, change "AAP4" to -- AAP-4 --.
Line 35, change "AAP4" to -- AAP-4 --.

Column 16,
Line 24, change "nyc" to -- myc --.

Column 51,
Line 46, change "encodes" to -- wherein said isolated or recombinant nucleic acid encodes --.

Signed and Sealed this

Third Day of January, 2006

JON W. DUDAS
*Director of the United States Patent and Trademark Office*

SEQUENCE LISTING

<160> NUMBER OF SEQ ID NOS: 18

<210> SEQ ID NO 1
<211> LENGTH: 873
<212> TYPE: DNA
<213> ORGANISM: Homo sapiens
<220> FEATURE:
<221> NAME/KEY: misc_feature
<223> OTHER INFORMATION: Description of Sequence: partial sequence of
      vector pMT2SM-AAP-2-

<400> SEQUENCE: 1

```
cccagacctc tggcatagag gagccttctg agacaaaggg ttctatgcaa aaaagcaaat      60
tcaaatataa gttggttcct gaagaagaaa ccactgcctc agaaaataca gagataacct     120
ctgaaaggca gaaagagggc atcaaattaa caatcaggat atcaagtcgg aaaagaagc     180 ccgattctcc ccccaaagtt ctagaaccag aaaacaagca agagaagaca gaaaaggaag     240
aggagaaaac aaatgtgggt cgtactttaa gaagatctcc aagaatatct agacccactg     300
caaaggtggc tgagatcaga gatcagaaag ctgataaaaa aagaggggaa ggagaagatg     360
aggtggaaga agagtcaaca gctttgcaaa aaactgacaa aaaggaaatt ttgaaaaaat     420
cagagaaaga tacaaattct aaagtaagca aggtaaaacc caaaggcaaa gttcgatgga     480
ctggttctcg gacacgtggc agatggaaat attccagcaa tgatgaaagt gaagggtctg     540
```

-continued

```
gcagtgaaaa atcatctgca gcttcagaag aggaggagga aaaggaaagt gaagaagcca      600
tcctagcaga tgatgatgaa ccatgcaaaa aatgtggcct tccaaaccat cctgagctaa      660
ttcttctgtg tgactcttgc gatagtggat accatactgc ctgccttcgc cctcctctga      720
tgatcatccc agatggagaa tggttctgcc caccttgcca acataaactg ctctgtgaaa      780
aattagagga acagttgcag gatttggatg ttgcccttaaa gaagaaagag cgtgccgaac     840
gaagaaaaga acgcttggtg tatgttggta tca                                   873
```

<210> SEQ ID NO 2
<211> LENGTH: 1150
<212> TYPE: DNA
<213> ORGANISM: Homo sapiens
<220> FEATURE:
<221> NAME/KEY: misc_feature
<223> OTHER INFORMATION: Description of sequence: partial sequence of
      vector pMT2SM-AAP-2-I

<400> SEQUENCE: 2

```
ccttttcttg ataaggacgc acaaagattg agtccaatac cagaagaagt tccaaagagt       60
actctagagt cagaaaagcc tggctctcct gaggcagctg aaacttctcc accatctaat      120
atcattgacc actgtgagaa actagcctca gaaaaagaag tggtagaatg ccagagtaca      180
agtactgttg gtggccagtc tgtgaaaaaa gtagacctag aaaccctaaa agaggattct      240
gagttcacaa aggtagaaat ggataatctg acaatgccc agacctctgg catagaggag      300
ccttctgaga caaagggttc tatgcaaaaa agcaaattca aatataagtt ggttcctgaa      360
gaagaaacca ctgcctcaga aaatacagag ataacctctg aaaggcagaa agagggcatc      420
aaattaacaa tcaggatatc aagtcggaaa agaagcccg attctccccc caaagttcta      480
gaaccagaaa acaagcaaga gaagacagaa aaggaagagg agaaaacaaa tgtgggtcgt      540
actttaagaa gatctccaag aatatctaga cccactgcaa aggtggctga atcagagat       600 cagaaagctg ataaaaaaag aggggaagga gaagatgagg tggaagaaga gtcaacagct      660
ttgcaaaaaa ctgacaaaaa ggaaattttg aaaaaatcag agaaagatac aaattctaaa      720
gtaagcaagg taaaacccaa aggcaaagtt cgatggactg gttctcggac acgtggcaga      780
tggaaatatt ccagcaatga tgaaagtgaa gggtctggca gtgaaaaatc atctgcagct      840
tcagaagagg aggaggaaaa ggaaagtgaa gaagccatcc tagcagatga tgatgaacca      900
tgcaaaaaat gtggccttcc aaaccatcct gagctaattc ttctgtgtga ctcttgcgat      960
agtggatacc atactgcctg ccttcgccct cctctgatga tcatcccaga tggagaatgg     1020
ttctgcccac cttgccaaca taaactgctc tgtgaaaaat tagaggaaca gttgcaggat     1080
ttggatgttg ccttaaagaa gaaagagcgt gccgaacgaa gaaagaacg cttggtgtat     1140 gttggtatca                                                            1150
```

<210> SEQ ID NO 3
<211> LENGTH: 386
<212> TYPE: PRT
<213> ORGANISM: Homo sapiens
<220> FEATURE:
<221> NAME/KEY: misc_feature
<223> OTHER INFORMATION: Description of Sequence: amino acid sequence of
      the analyzed region of the Apoptin-associating clone AAP-2-II
<221> NAME/KEY: misc_feature
<222> LOCATION: (1)..(3)
<223> OTHER INFORMATION: Description of Sequence: the three C-terminal
      amino acids (His-Glu-Gly) are from the multiple cloning site of
      pACT

<400> SEQUENCE: 3

```
His Glu Gly Pro Phe Leu Asp Lys Asp Ala Gln Arg Leu Ser Pro Ile
  1               5                  10                  15
Pro Glu Glu Val Pro Lys Ser Thr Leu Glu Ser Glu Lys Pro Gly Ser
             20                  25                  30
Pro Glu Ala Ala Glu Thr Ser Pro Pro Ser Asn Ile Ile Asp His Cys
         35                  40                  45
Glu Lys Leu Ala Ser Glu Lys Glu Val Val Glu Cys Gln Ser Thr Ser
     50                  55                  60
Thr Val Gly Gly Gln Ser Val Lys Lys Val Asp Leu Glu Thr Leu Lys
 65                  70                  75                  80
Glu Asp Ser Glu Phe Thr Lys Val Glu Met Asp Asn Leu Asp Asn Ala
                 85                  90                  95
Gln Thr Ser Gly Ile Glu Glu Pro Ser Glu Thr Lys Gly Ser Met Gln
            100                 105                 110
Lys Ser Lys Phe Lys Tyr Lys Leu Val Pro Glu Glu Thr Thr Ala
        115                 120                 125
Ser Glu Asn Thr Glu Ile Thr Ser Glu Arg Gln Lys Glu Gly Ile Lys
    130                 135                 140
Leu Thr Ile Arg Ile Ser Ser Arg Lys Lys Pro Asp Ser Pro Pro
145                 150                 155                 160
Lys Val Leu Glu Pro Glu Asn Lys Gln Glu Lys Thr Glu Lys Glu Glu
                165                 170                 175
Glu Lys Thr Asn Val Gly Arg Thr Leu Arg Arg Ser Pro Arg Ile Ser
            180                 185                 190
Arg Pro Thr Ala Lys Val Ala Glu Ile Arg Asp Gln Lys Ala Asp Lys
        195                 200                 205
Lys Arg Gly Glu Gly Glu Asp Glu Val Glu Glu Ser Thr Ala Leu
    210                 215                 220
Gln Lys Thr Asp Lys Lys Glu Ile Leu Lys Lys Ser Glu Lys Asp Thr
225                 230                 235                 240
Asn Ser Lys Val Ser Lys Val Lys Pro Lys Gly Lys Val Arg Trp Thr
                245                 250                 255
Gly Ser Arg Thr Arg Gly Arg Trp Lys Tyr Ser Ser Asn Asp Glu Ser
            260                 265                 270
Glu Gly Ser Gly Ser Glu Lys Ser Ala Ala Ser Glu Glu Glu Glu
        275                 280                 285
Glu Lys Glu Ser Glu Glu Ala Ile Leu Ala Asp Asp Glu Pro Cys
    290                 295                 300
Lys Lys Cys Gly Leu Pro Asn His Pro Glu Leu Ile Leu Leu Cys Asp
305                 310                 315                 320
Ser Cys Asp Ser Gly Tyr His Thr Ala Cys Leu Arg Pro Pro Leu Met
                325                 330                 335
Ile Ile Pro Asp Gly Glu Trp Phe Cys Pro Pro Cys Gln His Lys Leu
            340                 345                 350
Leu Cys Glu Lys Leu Glu Glu Gln Leu Gln Asp Leu Asp Val Ala Leu
        355                 360                 365
Lys Lys Lys Glu Arg Ala Glu Arg Arg Lys Glu Arg Leu Val Tyr Val
    370                 375                 380
Gly Ile
385
```

```
<210> SEQ ID NO 4
<211> LENGTH: 651
<212> TYPE: DNA
<213> ORGANISM: Homo sapiens
<220> FEATURE:
<221> NAME/KEY: misc_feature
<223> OTHER INFORMATION: Description of Sequence: partial sequence of
      vector pMT2SM-AAP-3

<400> SEQUENCE: 4
ccgatggtag gcggcggcgg ggtcggcggc ggcctcctgg agaatgccaa ccccctcatc    60
taccagcgct ctggggagcg gcctgtgacg gcaggcgagg aggacgagca ggttcccgac   120
agcatcgacg cacgcgagat cttcgarctg attcgctcca tcaatgaccc ggagcatcca   180
ctgacgctag aggagttgaa cgtagtagag caggtgcggg ttcaggttag cgaccccgag   240
agtacagtgg ctgtggcttt cacaccaacc attccgcact gcagcatggc cacccttatt   300
ggtctgtcca tcaaggtcaa gcttctgcgc tcccttcctc agcgtttcaa gatggacgtg   360
cacattactc cggggaccca tgcctcagag catgcagtga acaagcaact tgcagataag   420
gagcgggtgg cagctgccct ggagaacacc cacctcttgg aggttgtgaa tcagtgcctg   480
tcagcccgct cctgagcctg gccttgtgacc cctcaacctg catactgggt atcctggtcc   540
caactcctgc caagggctgt taccgttgtt ttcctggaat cactcacaaa tgagaaacta   600
acatttgcct ttttgtaata aagttaattt atattcaaaa aaaaaaaaa c             651

<210> SEQ ID NO 5
<211> LENGTH: 167
<212> TYPE: PRT
<213> ORGANISM: Homo sapiens
<220> FEATURE:
<221> NAME/KEY: misc_feature
<223> OTHER INFORMATION: Description of Sequence: amino acid sequence
      of the analyzed region of the Apoptin-associating clone AAP-4
<221> NAME/KEY: misc_feature
<223> OTHER INFORMATION: Description of Sequence: the three C-terminal
      amino acids (His-Glu-Gly) are from the multiple cloning site of
      pAC

<400> SEQUENCE: 5

His Glu Gly Pro Met Val Gly Gly Gly Val Gly Gly Leu Leu
1               5                   10                  15

Glu Asn Ala Asn Pro Leu Ile Tyr Gln Arg Ser Gly Glu Arg Pro Val
            20                  25                  30

Thr Ala Gly Glu Glu Asp Glu Gln Val Pro Asp Ser Ile Asp Ala Arg
        35                  40                  45

Glu Ile Phe Asp Leu Ile Arg Ser Ile Asn Asp Pro Glu His Pro Leu
    50                  55                  60

Thr Leu Glu Glu Leu Asn Val Val Glu Gln Val Arg Val Gln Val Ser
65                  70                  75                  80

Asp Pro Glu Ser Thr Val Ala Val Ala Phe Thr Pro Thr Ile Pro His
                85                  90                  95

Cys Ser Met Ala Thr Leu Ile Gly Leu Ser Ile Lys Val Lys Leu Leu
            100                 105                 110

Arg Ser Leu Pro Gln Arg Phe Lys Met Asp Val His Ile Thr Pro Gly
        115                 120                 125

Thr His Ala Ser Glu His Ala Val Asn Lys Gln Leu Ala Asp Lys Glu
    130                 135                 140

Arg Val Ala Ala Ala Leu Glu Asn Thr His Leu Leu Glu Val Val Asn
145                 150                 155                 160
```

Gln Cys Leu Ser Ala Arg Ser
            165

<210> SEQ ID NO 6
<211> LENGTH: 5331
<212> TYPE: DNA
<213> ORGANISM: Homo sapiens
<220> FEATURE:
<221> NAME/KEY: misc_feature
<223> OTHER INFORMATION: Description of Sequence: nucleic acid
      sequence of AAP-2
<221> NAME/KEY: misc_feature
<222> LOCATION: (3851)..(3900)
<223> OTHER INFORMATION: n is an unknown nucleotide

<400> SEQUENCE: 6

| | | | | | |
|---|---|---|---|---|---|
| ggcaagcccg | aagggaagga | gagaagggg | cggaaagagg | gcggaaagtg | aaaggcgccg | 60 |
| agggccgctc | tgtctcccgt | ctgactcggt | tctcgactgc | tccgggccgc | cgatgtattg | 120 |
| tgggatcgcg | gaccgtccct | gagacgctgg | gatccgcaga | ggagcccact | tgagagcgcc | 180 |
| tcctgtcgtc | tgtaaggttg | ccttgccatc | cctcggcacc | ccaacttccc | ccgcccccc | 240 |
| atcgcctcct | cctccatcct | ccagttcagg | cggcgcaggg | cggcggcacg | gcggcggtga | 300 |
| tggctcctcc | gggctgcccg | ggttcgtgcc | ccaacttcgc | cgtagtctgc | tccttcttgg | 360 |
| agcgctacgg | gccgctgcta | gacctgcctg | agttgccgtt | ccctgagctg | gagcgggtgc | 420 |
| tgcaggcgcc | gccgccggac | gtcggcaacg | gagaagtacc | aaaagaattg | gtggagctcc | 480 |
| atttgaagct | gatgaggaaa | attggcaaat | ctgttactgc | agacagatgg | gaaaaatatt | 540 |
| tgatcaagta | cctctgtgag | tgtcagtttg | atgacaatct | caaattcaag | aatattatta | 600 |
| atgaggagga | tgccgatact | atgcgtctcc | agccaattgg | tcgagacaaa | gatggcctca | 660 |
| tgtactggta | ccaattggat | caagatcaca | atgtcagaat | gtacatagaa | gaacaagatg | 720 |
| atcaagatgg | ctcttcatgg | aaatgcattg | tcagaaatcg | aaacgagttg | gctgagactc | 780 |
| ttgcactcct | gaaagcacaa | attgatcctg | tactattgaa | aaactctagc | caacaagaca | 840 |
| actcttctcg | ggaaagtccc | agcttagagg | atgaggagac | taaaaagag | gaagaaacac | 900 |
| ctaaacaaga | ggaacagaaa | gaaagtgaaa | agatgaaaag | tgaggagcag | cctatggatt | 960 |
| tagaaaaccg | ttctacagcc | aatgttctag | aagagactac | tgtgaaaaaa | gaaaagaag | 1020 |
| atgaaaagga | acttgtgaaa | ctgccagtca | tagtgaagct | agaaaaacct | ttgccagaaa | 1080 |
| atgaagaaaa | aaagattatc | aaagaagaaa | gtgattcctt | caaggaaaat | gtcaaaccca | 1140 |
| ttaaagttga | ggtgaaggaa | tgtagagcag | atcctaaaga | taccaaaagt | agcatggaga | 1200 |
| agccagtggc | acaggagcct | gaaaggatcg | aatttggtgg | caatattaaa | tcttctcacg | 1260 |
| aaattactga | gaaatctact | gaagaaactg | agaaacttaa | aaatgaccag | caggccaaga | 1320 |
| taccactaaa | aaaacgagaa | attaaactga | gtgatgattt | tgacagtcca | gtcaagggac | 1380 |
| cttttgtgtaa | atcagttact | ccaacaaaag | agttttttgaa | agatgaaata | aaacaagagg | 1440 |
| aagagacttg | taaaaggatc | tctacaatca | ctgctttggg | tcatgaaggg | aaacagctgg | 1500 |
| taaatggaga | agttagtgat | gaaagggtag | ctccaaattt | taagacagaa | ccaatagaga | 1560 |
| caaagtttta | tgagacaaag | gaagagagct | atagcccctc | taaggacaga | aatatcatca | 1620 |
| cggagggaaa | tggaacagag | tccttaaatt | ctgtcataac | aagtatgaaa | acaggtgagc | 1680 |
| ttgagaaaga | aacagcccct | ttgaggaaag | atgcagatag | ttcaatatca | gtcttagaga | 1740 |
| tccatagtca | aaaagcacaa | atagaggaac | ccgatcctcc | agaaatggaa | acttctcttg | 1800 |
| attcttctga | gatggcaaaa | gatctctctt | caaaaactgc | tttatcttcc | accgagtcgt | 1860 |

-continued

```
gtaccatgaa aggtgaagag aagtctccca aaactaagaa ggataagcgc ccaccaatcc    1920
tagaatgtct tgaaaagtta gagaagtcca aaaagacttt tcttgataag gacgcacaaa    1980
gattgagtcc aataccagaa gaagttccaa agagtactct agagtcagaa aagcctggct    2040
ctcctgaggc agctgaaact tctccaccat ctaatatcat tgaccactgt gagaaactag    2100
cctcagaaaa agaagtggta gaatgccaga gtacaagtac tgttggtggc cagtctgtga    2160
aaaaagtaga cctagaaacc ctaaaagagg attctgagtt cacaaaggta gaaatggata    2220
atctggacaa tgcccagacc tctggcatag aggagcettc tgagacaaag ggttctatgc    2280
aaaaaagcaa attcaaatat aagttggttc ctgaagaaga aaccactgcc tcagaaaata    2340
cagagataac ctctgaaagg cagaagagg gcatcaaatt aacaatcagg atatcaagtc    2400
ggaaaaagaa gcccgattct ccccccaaag ttctagaacc agaaaacaag caagagaaga    2460
cagaaaagga agaggagaaa acaaatgtgg gtcgtacttt aagaagatct ccaagaatat    2520
ctagacccac tgcaaaagtg gctgagatca gagatcagaa agctgataaa aaagaggggg    2580
aaggagaaga tgaggtggaa gaagagtcaa cagctttgca aaaactgac aaaaaggaaa    2640
ttttgaaaaa atcagagaaa gatacaaatt ctaaagtaag caaggtaaaa cccaaaggca    2700
aagttcgatg gactggttct cggacacgtg gcagatggaa atattccagc aatgatgaaa    2760
gtgaagggtc tggcagtgaa aaatcatctg cagcttcaga agaggaggaa gaaaaggaaa    2820
gtgaagaagc catcctagca gatgatgatg aaccatgcaa aaaatgtggc cttccaaacc    2880
atcctgagct aattcttctg tgtgactctt gcgatagtgg ataccatact gcctgccttc    2940
gccctcctct gatgatcatc ccagatggag aatggttctg cccaccttgc aacataaac    3000
tgctctgtga aaaattagag gaacagttgc aggatttgga tgttgcctta agaagaaag    3060
agcgtgccga acgaagaaaa gaacgcttgg tgtatgttgg tatcagtatt gaaaacatca    3120
ttcctccaca agagccagac tttctgaagg atcaagaaga aaagaaaaaa gattcaaaaa    3180
aatccaaagc aaacttgctt gaaaggaggt caacaagaac aaggaaatgt ataagctaca    3240
gatttgatga gtttgatgaa gcaattgatg aagctattga agatgacatc aaagaagccg    3300
atggaggagg agttggccga ggaaaagata tctccaccat cacaggtcat cgtgggaaag    3360
acatctctac tattttggat gaagaaagaa aagaaaataa acgacccag ggcagctg     3420
ctgctcgaag gaagaaacgc cggcgattaa atgatctgga cagtgatagc aacctggatg    3480
aagaagagag cgaggatgaa ttcaagatca gtgatggatc tcaagatgag tttgttgtgt    3540
ctgatgaaaa cccagatgaa agtgaagaag atccgccatc taatgatgac agtgacactg    3600
acttttgtag ccgtagactg aggcgacacc cctctcggcc aatgaggcag agcaggcgtt    3660
tgcgaagaaa gaccccaaag aaaaaatatt ccgatgatga tgaagaggag gaatctgagg    3720
agaatagtag agactctgaa agtgacttca gtgatgattt tagtgatgat tttgtagaaa    3780
ctcggcgaag gcggtcaagg agaaatcaga aaagacaaat taactacaaa gaagactcag    3840
aaagtgacgg nnnnnnnnnn nnnnnnnnnn nnnnnnnnnn nnnnnnnnnn nnnnnnnnnn    3900
gaagactttc cagctcagag agtgaagaga gctatttgtc caagaactct gaagatgatg    3960
agctagctaa agaatcaaag cggtcagttc gaaagcgggg ccgaagcaca gacgagtatt    4020
cagaagcaga tgaggaggag gaggaagagg aaggcaaacc atcccgcaaa cggctacacc    4080
ggattgagac ggatgaggag gagagttgtg acaatgctca tggagatgca aatcagcctg    4140
cccgtgacag ccagcctagg gtcctgccct cagaacaaga gagcaccaag aagccctacc    4200
```

-continued

```
ggatagaaag tgatgaggaa gaggactttg aaaatgtagg caaagtgggg agcccattgg      4260
actatagctt agtggactta ccttcaacca atggacagag ccctggcaaa gccattgaga      4320
acttgattgg caagcctact gagaagtctc agaccccccaa ggacaacagc acagccagtg    4380
caagcctagc ctccaatggg acaagtggtg ggcaggaggc aggagcacca gaagaggagg      4440
aagatgagct tttgagagtg actgaccttg ttgattatgt ctgtaacagt gaacagttat      4500 aagactttt ttccattttt gtgctaattt attccacggt agctctcaca ccagcgggcc       4560
agttattaaa agctgtttaa ttttccctag aaaactccac tacagaatga cttttagaag      4620
aaaaatttca acaaatcctg aagtctttct gtgaagtgac cagttctgaa cttgaagat       4680 aaataattgc tgtaaattcc ttttgatttt ctttttccag gttcatggtc cttggtaatt      4740
tcattcatgg aaaaaaatct tattataata acaacaaaga tttgtatatt tttgacttta    4800
tatttcctga gctctcctga ctttgtgaaa aagggtggat gaaaatgcat tccgaatctg      4860
tgagggccca aaacagaatt tagggtgtgg tgaaagcact tgtgctttag cttttcata      4920 ttaaatatat attatattta aacattcatg gcatagatga tgatttacag acaatttaaa      4980
agttcaagtc tgtactgtta cagtttgaga attgtagata acatcataca taagtcattt      5040
agtaacagcc tttgtgaaat gaacttgttt actattggag ataaccacac ttaataaaga      5100
agagacagtg aaagtaccat cataattaac ctaaattttt gttatagcag agtttcttgt      5160
ttaaaaaaaa ataaaatcat ctgaaaagca aaaatacagt aaaatgtata atgaagcttt      5220
gccaaccaga ctgtgctagc aacaaatttt tttaaataag ctttatgcag tggtaataag      5280
gtggcctcaa atatattgtg tctgatggag agttattagt gaaatgaatg t              5331
```

<210> SEQ ID NO 7
<211> LENGTH: 1400
<212> TYPE: PRT
<213> ORGANISM: Homo sapiens
<220> FEATURE:
<221> NAME/KEY: misc_feature
<223> OTHER INFORMATION: Description of Sequence: Amino acid sequence
      deduced from the nucleic acid seqeuence of AAP-4

<400> SEQUENCE: 7

```
Met Ala Pro Pro Gly Cys Pro Gly Ser Cys Pro Asn Phe Ala Val Val
1               5                   10                  15

Cys Ser Phe Leu Glu Arg Tyr Gly Pro Leu Leu Asp Leu Pro Glu Leu
                20                  25                  30

Pro Phe Pro Glu Leu Glu Arg Val Leu Gln Ala Pro Pro Asp Val
            35                  40                  45

Gly Asn Gly Glu Val Pro Lys Glu Leu Val Glu Leu His Leu Lys Leu
        50                  55                  60

Met Arg Lys Ile Gly Lys Ser Val Thr Ala Asp Arg Trp Glu Lys Tyr
65                  70                  75                  80

Leu Ile Lys Tyr Leu Cys Glu Cys Gln Phe Asp Asn Leu Lys Phe
                85                  90                  95

Lys Asn Ile Ile Asn Glu Glu Asp Ala Asp Thr Met Arg Leu Gln Pro
                100                 105                 110

Ile Gly Arg Asp Lys Asp Gly Leu Met Tyr Trp Tyr Gln Leu Asp Gln
            115                 120                 125

Asp His Asn Val Arg Met Tyr Ile Glu Glu Gln Asp Gln Asp Gly
        130                 135                 140

Ser Ser Trp Lys Cys Ile Val Arg Asn Arg Asn Glu Leu Ala Glu Thr
145                 150                 155                 160
```

```
Leu Ala Leu Leu Lys Ala Gln Ile Asp Pro Val Leu Lys Asn Ser
            165                 170                 175

Ser Gln Gln Asp Asn Ser Ser Arg Glu Ser Pro Ser Leu Glu Asp Glu
            180                 185                 190

Glu Thr Lys Lys Glu Glu Thr Pro Lys Gln Glu Gln Lys Glu
            195                 200                 205

Ser Glu Lys Met Lys Ser Glu Gln Pro Met Asp Leu Glu Asn Arg
    210                 215                 220

Ser Thr Ala Asn Val Leu Glu Glu Thr Thr Val Lys Glu Lys Glu
225                 230                 235                 240

Asp Glu Lys Glu Leu Val Lys Leu Pro Val Ile Val Lys Leu Glu Lys
            245                 250                 255

Pro Leu Pro Glu Asn Glu Glu Lys Lys Ile Ile Lys Glu Glu Ser Asp
            260                 265                 270

Ser Phe Lys Glu Asn Val Lys Pro Ile Lys Val Glu Val Lys Glu Cys
    275                 280                 285

Arg Ala Asp Pro Lys Asp Thr Lys Ser Ser Met Glu Lys Pro Val Ala
290                 295                 300

Gln Glu Pro Glu Arg Ile Glu Phe Gly Gly Asn Ile Lys Ser Ser His
305                 310                 315                 320

Glu Ile Thr Glu Lys Ser Thr Glu Glu Thr Glu Lys Leu Lys Asn Asp
            325                 330                 335

Gln Gln Ala Lys Ile Pro Leu Lys Lys Arg Glu Ile Lys Leu Ser Asp
            340                 345                 350

Asp Phe Asp Ser Pro Val Lys Gly Pro Leu Cys Lys Ser Val Thr Pro
            355                 360                 365

Thr Lys Glu Phe Leu Lys Asp Glu Ile Lys Gln Glu Glu Thr Cys
    370                 375                 380

Lys Arg Ile Ser Thr Ile Thr Ala Leu Gly His Glu Gly Lys Gln Leu
385                 390                 395                 400

Val Asn Gly Glu Val Ser Asp Glu Arg Val Ala Pro Asn Phe Lys Thr
            405                 410                 415

Glu Pro Ile Glu Thr Lys Phe Tyr Glu Thr Lys Glu Glu Ser Tyr Ser
            420                 425                 430

Pro Ser Lys Asp Arg Asn Ile Ile Thr Glu Gly Asn Gly Thr Glu Ser
            435                 440                 445

Leu Asn Ser Val Ile Thr Ser Met Lys Thr Gly Glu Leu Glu Lys Glu
            450                 455                 460

Thr Ala Pro Leu Arg Lys Asp Ala Asp Ser Ser Ile Ser Val Leu Glu
465                 470                 475                 480

Ile His Ser Gln Lys Ala Gln Ile Glu Glu Pro Asp Pro Pro Glu Met
            485                 490                 495

Glu Thr Ser Leu Asp Ser Ser Glu Met Ala Lys Asp Leu Ser Ser Lys
            500                 505                 510

Thr Ala Leu Ser Ser Thr Glu Ser Cys Thr Met Lys Gly Glu Glu Lys
            515                 520                 525

Ser Pro Lys Thr Lys Lys Asp Lys Arg Pro Ile Leu Glu Cys Leu
    530                 535                 540

Glu Lys Leu Glu Lys Ser Lys Lys Thr Phe Leu Asp Lys Asp Ala Gln
545                 550                 555                 560

Arg Leu Ser Pro Ile Pro Glu Glu Val Pro Lys Ser Thr Leu Glu Ser
            565                 570                 575
```

-continued

```
Glu Lys Pro Gly Ser Pro Glu Ala Ala Glu Thr Ser Pro Pro Ser Asn
            580                 585                 590

Ile Ile Asp His Cys Glu Lys Leu Ala Ser Glu Lys Glu Val Val Glu
            595                 600                 605

Cys Gln Ser Thr Ser Thr Val Gly Gly Gln Ser Val Lys Lys Val Asp
            610                 615                 620

Leu Glu Thr Leu Lys Glu Asp Ser Glu Phe Thr Lys Val Glu Met Asp
625                 630                 635                 640

Asn Leu Asp Asn Ala Gln Thr Ser Gly Ile Glu Glu Pro Ser Glu Thr
                645                 650                 655

Lys Gly Ser Met Gln Lys Ser Lys Phe Lys Tyr Lys Leu Val Pro Glu
                660                 665                 670

Glu Glu Thr Thr Ala Ser Glu Asn Thr Glu Ile Thr Ser Glu Arg Gln
                675                 680                 685

Lys Glu Gly Ile Lys Leu Thr Ile Arg Ile Ser Ser Arg Lys Lys Lys
            690                 695                 700

Pro Asp Ser Pro Pro Lys Val Leu Glu Pro Glu Asn Lys Gln Glu Lys
705                 710                 715                 720

Thr Glu Lys Glu Glu Glu Lys Thr Asn Val Gly Arg Thr Leu Arg Arg
                725                 730                 735

Ser Pro Arg Ile Ser Arg Pro Thr Ala Lys Val Ala Glu Ile Arg Asp
                740                 745                 750

Gln Lys Ala Asp Lys Lys Arg Gly Glu Gly Glu Asp Glu Val Glu Glu
            755                 760                 765

Glu Ser Thr Ala Leu Gln Lys Thr Asp Lys Lys Glu Ile Leu Lys Lys
            770                 775                 780

Ser Glu Lys Asp Thr Asn Ser Lys Val Ser Lys Val Lys Pro Lys Gly
785                 790                 795                 800

Lys Val Arg Trp Thr Gly Ser Arg Thr Arg Gly Arg Trp Lys Tyr Ser
                805                 810                 815

Ser Asn Asp Glu Ser Glu Gly Ser Glu Lys Ser Ser Ala Ala
                820                 825                 830

Ser Glu Glu Glu Glu Lys Glu Glu Ala Ile Leu Ala Asp
            835                 840                 845

Asp Asp Glu Pro Cys Lys Lys Cys Gly Leu Pro Asn His Pro Glu Leu
850                 855                 860

Ile Leu Leu Cys Asp Ser Cys Asp Ser Gly Tyr His Thr Ala Cys Leu
865                 870                 875                 880

Arg Pro Pro Leu Met Ile Ile Pro Asp Gly Glu Trp Phe Cys Pro Pro
                885                 890                 895

Cys Gln His Lys Leu Leu Cys Glu Lys Leu Glu Glu Gln Leu Gln Asp
                900                 905                 910

Leu Asp Val Ala Leu Lys Lys Lys Glu Arg Ala Glu Arg Arg Lys Glu
            915                 920                 925

Arg Leu Val Tyr Val Gly Ile Ser Ile Glu Asn Ile Ile Pro Pro Gln
930                 935                 940

Glu Pro Asp Phe Ser Glu Asp Gln Glu Glu Lys Lys Asp Ser Lys
945                 950                 955                 960

Lys Ser Lys Ala Asn Leu Leu Glu Arg Arg Ser Thr Arg Thr Arg Lys
                965                 970                 975

Cys Ile Ser Tyr Arg Phe Asp Glu Phe Asp Glu Ala Ile Asp Glu Ala
                980                 985                 990

Ile Glu Asp Asp Ile Lys Glu Ala  Asp Gly Gly Gly Val  Gly Arg Gly
```

-continued

```
                995                  1000                 1005
Lys Asp Ile Ser Thr Ile Thr Gly His Arg Gly Lys Asp Ile Ser
         1010                1015                1020

Thr Ile Leu Asp Glu Glu Arg Lys Glu Asn Lys Arg Pro Gln Arg
         1025                1030                1035

Ala Ala Ala Ala Arg Arg Lys Lys Arg Arg Leu Asn Asp Leu
         1040                1045                1050

Asp Ser Asp Ser Asn Leu Asp Glu Glu Glu Ser Glu Asp Glu Phe
         1055                1060                1065

Lys Ile Ser Asp Gly Ser Gln Asp Glu Phe Val Val Ser Asp Glu
         1070                1075                1080

Asn Pro Asp Glu Ser Glu Glu Asp Pro Pro Ser Asn Asp Asp Ser
         1085                1090                1095

Asp Thr Asp Phe Cys Ser Arg Arg Leu Arg Arg His Pro Ser Arg
         1100                1105                1110

Pro Met Arg Gln Ser Arg Arg Leu Arg Arg Lys Thr Pro Lys Lys
         1115                1120                1125

Lys Tyr Ser Asp Asp Asp Glu Glu Glu Ser Glu Glu Asn Ser
         1130                1135                1140

Arg Asp Ser Glu Ser Asp Phe Ser Asp Asp Phe Ser Asp Asp Phe
         1145                1150                1155

Val Glu Thr Arg Arg Arg Arg Ser Arg Arg Asn Gln Lys Arg Gln
         1160                1165                1170

Ile Asn Tyr Lys Glu Asp Ser Glu Ser Asp Gly Ser Gln Lys Ser
         1175                1180                1185

Leu Arg Arg Gly Lys Glu Ile Arg Arg Val His Lys Arg Arg Leu
         1190                1195                1200

Ser Ser Ser Glu Ser Glu Glu Ser Tyr Leu Ser Lys Asn Ser Glu
         1205                1210                1215

Asp Asp Glu Leu Ala Lys Glu Ser Lys Arg Ser Val Arg Lys Arg
         1220                1225                1230

Gly Arg Ser Thr Asp Glu Tyr Ser Glu Ala Asp Glu Glu Glu Glu
         1235                1240                1245

Glu Glu Glu Gly Lys Pro Ser Arg Lys Arg Leu His Arg Ile Glu
         1250                1255                1260

Thr Asp Glu Glu Glu Ser Cys Asp Asn Ala His Gly Asp Ala Asn
         1265                1270                1275

Gln Pro Ala Arg Asp Ser Gln Pro Arg Val Leu Pro Ser Glu Gln
         1280                1285                1290

Glu Ser Thr Lys Lys Pro Tyr Arg Ile Glu Ser Asp Glu Glu Glu
         1295                1300                1305

Asp Phe Glu Asn Val Gly Lys Val Gly Ser Pro Leu Asp Tyr Ser
         1310                1315                1320

Leu Val Asp Leu Pro Ser Thr Asn Gly Gln Ser Pro Gly Lys Ala
         1325                1330                1335

Ile Glu Asn Leu Ile Gly Lys Pro Thr Glu Lys Ser Gln Thr Pro
         1340                1345                1350

Lys Asp Asn Ser Thr Ala Ser Ala Ser Leu Ala Ser Asn Gly Thr
         1355                1360                1365

Ser Gly Gly Gln Glu Ala Gly Ala Pro Glu Glu Glu Asp Glu
         1370                1375                1380

Leu Leu Arg Val Thr Asp Leu Val Asp Tyr Val Cys Asn Ser Glu
         1385                1390                1395
```

```
Gln Leu
    1400

<210> SEQ ID NO 8
<211> LENGTH: 46
<212> TYPE: PRT
<213> ORGANISM: Homo sapiens
<220> FEATURE:
<221> NAME/KEY: misc_feature
<223> OTHER INFORMATION: Description of Sequence: PHD-finger domain of
      the AAP-2 proetin

<400> SEQUENCE: 8

Glu Pro Cys Lys Lys Cys Gly Leu Pro Asn His Pro Glu Leu Ile Leu
1               5                   10                  15

Leu Cys Asp Ser Cys Asp Ser Gly Tyr His Thr Ala Cys Leu Arg Pro
            20                  25                  30

Pro Leu Met Ile Ile Pro Asp Gly Glu Trp Phe Cys Pro Pro
        35                  40                  45

<210> SEQ ID NO 9
<211> LENGTH: 5690
<212> TYPE: DNA
<213> ORGANISM: Homo sapiens
<220> FEATURE:
<221> NAME/KEY: misc_feature
<223> OTHER INFORMATION: Description of Sequence: nucleic acid sequence
      of AAP-4

<400> SEQUENCE: 9
cggcagggca gcggggcgat gaggtgagga cgcccgggaa ccggaggcgg caccgcgcgg      60
cgcacggacc tgggacgcgg agtcctgaag ccggcggacg gttttcgtac gggcggccgt    120
gcgcgaggcg aggagagaac attgaaagta ttctctaagc tatttgaaga gagtgactaa    180
atgcacctgg gtcaggctgt ctgtgggtat gaagtggttg ggagaatcca agaacatggt    240
ggtgaatggc aggagaaatg gaggcaagtt gtctaatgac catcagcaga atcaatcaaa    300
attacagcac acggggaagg acaccctgaa ggctggcaaa aatgcagtcg agaggaggtc    360
gaacagatgt aatggtaact cgggatttga aggacagagt cgctatgtac catcctctgg    420
aatgtccgcc aaggaactct gtgaaaatga tgacctagca accagtttgg ttcttgatcc    480
ctatttaggt tttcaaacac acaaaatgaa tactagcgcc tttccttcga ggagctcaag    540
gcatttttca aaatctgaca gttttttctca caacaaccct gtgagattta ggcctattaa    600
aggaaggcag gaagaactaa aggaagtaat tgaacgtttt aagaaagatg aacacttgga    660
gaaagccttc aaatgtttga cttcaggcga atgggcacgg cactattttc tcaacaagaa    720
taaaatgcag gagaaattat tcaaagaaca tgtatttatt tatttgcgaa tgtttgcaac    780
tgacagtgga tttgaaatat tgccatgtaa tagatactca tcagaacaaa atggagccaa    840
aatagttgca acaaaagagt ggaaacgaaa tgacaaaata gaattactgg tgggttgtat    900
tgccgaactt tcagaaattg aggagaacat gctacttaga catggagaaa acgacttcag    960
tgtcatgtac tccacaagga aaaactgtgc tcaactctgg ctgggtcctg ctgcgtttat   1020
aaaccatgat tgcagaccta attgtaagtt tgtgtcaact ggtcgagata cagcatgtgt   1080
gaaggctcta agagacattg aacctggaga agaaattcct tgttattatg agatgggtt    1140 ctttggagaa aataatgagt ctgcgagtg ttacacttgc gaaagacggg gcactggtgc   1200
ttttaaatcc agagtgggac tgcctgcgcc tgctcctgtt atcaatagca aatatggact   1260
```

-continued

```
cagagaaaca gataaacgtt taaataggct taaaaagtta ggtgacagca gcaaaaattc   1320
agacagtcaa tctgtcagct ctaacactga tgcagatacc actcaggaaa aaacaatgc    1380
aacttctaac cgaaaatctt cagttggcgt aaaaaagaat agcaagagca gaacgttaac   1440
gaggcaatct atgtcaagaa ttccagcttc ttccaactct acctcatcta agctaactca   1500
tataaataat tccagggtac caagaaaact gaagaagcct gcaaagcctt tactttcaaa   1560
gataaaattg agaaatcatt gcaagcggct ggagcaaaag aatgcttcaa gaaaactcga   1620
aatgggaaac ttagtactga agagcctaa agtagttctg tataaaaatt tgcccattaa    1680
aaaagataag gagccagagg gaccagccca agccgcagtt gccagcgggt gcttgactag   1740
acacgcggcg agagaacaca gacagaatcc tgtgagaggt gctcattcgc aggggagag    1800
ctcgccctgc acctacataa ctcggcggtc agtgaggaca agaacaaatc tgaaggaggc   1860
ctctgacatc aagcttgaac caaatacgtt gaatggctat aaaagcagtg tgacggaacc   1920
ttgccccgac agtggtgaac agctgcagcc agctcctgtg ctgcaggagg aagaactggc   1980
tcatgagact gcacaaaaag gggaggcaaa gtgtcataag agtgacacag gcatgtccaa   2040
aaagaagtca cgacaaggaa aacttgtgaa acagtttgca aaaatagagg aatctactcc   2100
agtgcacgat tctcctggaa aagacgacgc ggtaccagat ttgatgggtc cccattctga   2160
ccagggtgag cacagtggca ctgtgggcgt gcctgtgagc tacacagact gtgctccttc   2220
acccgtcggt tgttcagttg tgacatcaga tagcttcaaa acaaaagaca gctttagaac   2280
tgcaaaaagt aaaagaaga ggcgaatcac aaggtatgat gcacagttaa tcctagaaaa     2340
taactctggg attcccaaat tgactcttcg taggcgtcat gatagcagca gcaaaacaaa   2400
tgaccaagag aatgatggaa tgaactcttc caaataagc atcaagttaa gcaaagacca    2460
tgacaacgat aacaatctct atgtagcaaa gcttaataat ggatttaact caggatcagg   2520
cagtagttct acaaaattaa aaatccagct aaaacgagat gaggaaaata gggggtctta    2580
tacagagggg cttcatgaaa atggggtgtg ctgcagtgat cctcttttctc tcttggagtc   2640
tcgaatggag gtggatgact atagtcagta tgaggaagaa agtacagatg attcctcctc    2700
ttctgagggc gatgaagagg aggatgacta tgatgatgac tttgaagacg attttattcc   2760
tcttcctcca gctaagcgct tgaggttaat agttggaaaa gactctatag atattgacat   2820
ttcttcaagg agaagagaag atcagtcttt aaggcttaat gcctaagctc ttggtcttaa   2880
cttgacctgg gataactact ttaaagaaat aaaaaattcc agtcaattat tcctcaactg   2940
aaagtttagt ggcagcactt ctattgtccc ttcacttatc agcatactat tgtagaaagt   3000
gtacagcata ctgactcaat tcttaagtct gatttgtgca aatttttatc gtactttta     3060
aatagccttc ttacgtgcaa ttctgagtta gaggtaaagc cctgttgtaa aataaaggct   3120
caagcaaaat tgtacagtga tagcaacttt ccacacagga cgttgaaaac agtaatgtgg   3180
ctacacagtt tttttaactg taagagcatc agctggctct ttaatatatg actaaacaat   3240
aatttaaaac aaatcatagt agcagcatat taagggtttc tagtatgcta atatcaccag   3300
caatgatctt tggcttttg atttatttgc tagatgtttc cccctggag ttttgtcagt      3360
ttcacactgt tgctggccc aggtgtactg tttgtggcct tgttaatat cgcaaaccat      3420
tggttgggag tcagattggt ttcttaaaaa aaaaaaaaa atgacatacg tgacagctca    3480
cttttcagtt cattatatgt acgagggtag cagtgtgtgg gatgaggttc gatacagcgt   3540
atttattgct tgtcatgtaa attaaaaacc ttgtatttaa ctcttttcaa tcctttaga     3600
taaaattgtt ctttgcaaga atgattggtg cttattttt caaaaatttg ctgtgaacaa     3660
```

-continued

```
cgtgatgaca acaagcaaca tttatctaat gaactacagc tatcttaatt tggttcttca    3720
agttttctgt tgcacttgta aaatgctaca aggaatatta aaaaaatcta ttcactttaa    3780
cttataatag tttatgaaat aaaaacatga gtcacagctt tgttctgtg  gtaacctata    3840
aaaaagttt  gtctttgaga ttcaatgtaa agaactgaaa acaatgtata tgttgtaaat    3900
atttgtgtgt tgtgagacat ttttgtcata agaaattaaa agaacttacc aggaaggttt    3960
ttaagtttag aaatattcat gccaataaaa taggaaatta taaatatata gttttaagca    4020
ctgcatcagt gggagttctt ggcttatgtt agtttatgtt agtttattat gaaaacatca    4080
aagatttttt tgactatatt atcagttaaa caaaaaggag tcagatttaa tttgtttttt    4140
gaagcacttt gagaaattaa ttttaattaa cttaatgagc aaatttttat tactacttta    4200
tgttcaatac caggttcttt tcatttctct ggattatttt gcaaatcatt ggacagagaa    4260
tttgggaata taaatctgta acaggtgttg acaccagtag gtctctttat ttctgggaaa    4320
tgtgtacctg tactttctga tatacagtgt tcctaagtaa aaatcaattc aggggatttg    4380
tatagtgtct ataggaaagt agcccatgtc ttgaaatatg aaaaggaatc tgaaggtcat    4440
gaaaagtcca gtggagaaaa tctcaatgct tactgttact actaattgat tcctactagt    4500
ttccaggttt gggggggatat tgtttcaatg acgctcctta agactgttga ttgcccatag    4560
gttccaaata gaaattaaga ctcatgaaca tttttagaaa gtagattgtt ttctcctggt    4620
tctctaagga actacttctg cagtcttaca tagtctcatc cttgtttgtt gtggtgcagt    4680
cgaactcctc aggcgtttgg aaagcatgtg gtagaccttc ttccacaccc acccatacccc   4740
ccgttcactg cgtctggagg tcttcaacag tgaagtaggg cagcccacac agcctctcag    4800
gagcacctgt ccgaggcacc cggagcactt tgcagagcac gtccagccct catgggtcc    4860
ctgcatagaa atgtgaaccc ctgccactga ggaagatgaa ggtagaccct gtgtctggag    4920
gtgctggagg gcagcgggtc acctcttgta ttcccacctt agtttggggt gttttgaaga    4980
ggttcagaga ctaaatctta aaccttattt gaataccaac gatagctatt ttgggaattt    5040
cgatcttaaa aagtgacaaa acacatttcc cattttcatt tttcagctga attttagtaa    5100
cttattttg  atgttttaat tttatcatgg cctcctcttt ggaggccaac cttcccatgg    5160
gtctcaaagc agtgacattt ggtagtaaat cactgcctct caggagtcgg tatgcacaag    5220
cactcagcag ccactgttga tgccttctag ggaaacctaa tttccgttgg taaaggtagg    5280
ggcctcggaa ctgttccgga tctgctgtag aacttcaccg tgtggaatgg tgacagccac    5340
acaccgttga ccagtttaga agaggttgca ttcaataaaa ctcttagctt gagcttatgc    5400
aatgattggt taagattttg gcattgtaag aattaggaga tgatcataga aatatatgta    5460
aagtattcaa ttttcaatca ttttcaaatt actgttataa attgttttg  ctgagttgta    5520
atacttttga gatacaatgt attccttgta ctgaaagaat gaaaaggac  tttttcagca    5580
tttgaggtaa gttctttaac gtttcattaa aaacattttt tacaaatatt ttgtacatgc    5640
acttgcagta ttgaggttaa tcattttaat aaattcggaa attaaaaaaa              5690
```

<210> SEQ ID NO 10
<211> LENGTH: 876
<212> TYPE: PRT
<213> ORGANISM: Homo sapiens
<220> FEATURE:
<221> NAME/KEY: misc_feature
<223> OTHER INFORMATION: Description of Sequence: Amino acid sequence
       deduced from the nucleic acid seqeuence of AAP-4

<400> SEQUENCE: 10

```
Met Val Val Asn Gly Arg Arg Asn Gly Gly Lys Leu Ser Asn Asp His
  1               5                  10                  15

Gln Gln Asn Gln Ser Lys Leu Gln His Thr Gly Lys Asp Thr Leu Lys
             20                  25                  30

Ala Gly Lys Asn Ala Val Glu Arg Arg Ser Asn Arg Cys Asn Gly Asn
             35                  40                  45

Ser Gly Phe Glu Gly Gln Ser Arg Tyr Val Pro Ser Ser Gly Met Ser
     50                  55                  60

Ala Lys Glu Leu Cys Glu Asn Asp Leu Ala Thr Ser Leu Val Leu
 65                  70                  75                  80

Asp Pro Tyr Leu Gly Phe Gln Thr His Lys Met Asn Thr Ser Ala Phe
                 85                  90                  95

Pro Ser Arg Ser Ser Arg His Phe Ser Lys Ser Asp Ser Phe Ser His
                100                 105                 110

Asn Asn Pro Val Arg Phe Arg Pro Ile Lys Gly Arg Gln Glu Glu Leu
                115                 120                 125

Lys Glu Val Ile Glu Arg Phe Lys Lys Asp Glu His Leu Glu Lys Ala
130                 135                 140

Phe Lys Cys Leu Thr Ser Gly Glu Trp Ala Arg His Tyr Phe Leu Asn
145                 150                 155                 160

Lys Asn Lys Met Gln Glu Lys Leu Phe Lys Glu His Val Phe Ile Tyr
                165                 170                 175

Leu Arg Met Phe Ala Thr Asp Ser Gly Phe Glu Ile Leu Pro Cys Asn
                180                 185                 190

Arg Tyr Ser Ser Glu Gln Asn Gly Ala Lys Ile Val Ala Thr Lys Glu
                195                 200                 205

Trp Lys Arg Asn Asp Lys Ile Glu Leu Leu Val Gly Cys Ile Ala Glu
                210                 215                 220

Leu Ser Glu Ile Glu Glu Asn Met Leu Leu Arg His Gly Glu Asn Asp
225                 230                 235                 240

Phe Ser Val Met Tyr Ser Thr Arg Lys Asn Cys Ala Gln Leu Trp Leu
                245                 250                 255

Gly Pro Ala Ala Phe Ile Asn His Asp Cys Arg Pro Asn Cys Lys Phe
                260                 265                 270

Val Ser Thr Gly Arg Asp Thr Ala Cys Val Lys Ala Leu Arg Asp Ile
                275                 280                 285

Glu Pro Gly Glu Glu Ile Ser Cys Tyr Tyr Gly Asp Gly Phe Phe Gly
                290                 295                 300

Glu Asn Asn Glu Phe Cys Glu Cys Tyr Thr Cys Glu Arg Arg Gly Thr
305                 310                 315                 320

Gly Ala Phe Lys Ser Arg Val Gly Leu Pro Ala Pro Ala Pro Val Ile
                325                 330                 335

Asn Ser Lys Tyr Gly Leu Arg Glu Thr Asp Lys Arg Leu Asn Arg Leu
                340                 345                 350

Lys Lys Leu Gly Asp Ser Ser Lys Asn Ser Asp Ser Gln Ser Val Ser
                355                 360                 365

Ser Asn Thr Asp Ala Asp Thr Thr Gln Glu Lys Asn Asn Ala Thr Ser
                370                 375                 380

Asn Arg Lys Ser Ser Val Gly Val Lys Lys Asn Ser Lys Ser Arg Thr
385                 390                 395                 400

Leu Thr Arg Gln Ser Met Ser Arg Ile Pro Ala Ser Ser Asn Ser Thr
                405                 410                 415
```

-continued

```
Ser Ser Lys Leu Thr His Ile Asn Asn Ser Arg Val Pro Lys Lys Leu
        420                 425                 430

Lys Lys Pro Ala Lys Pro Leu Leu Ser Lys Ile Lys Leu Arg Asn His
        435                 440                 445

Cys Lys Arg Leu Glu Gln Lys Asn Ala Ser Arg Lys Leu Glu Met Gly
        450                 455                 460

Asn Leu Val Leu Lys Glu Pro Lys Val Val Leu Tyr Lys Asn Leu Pro
465                 470                 475                 480

Ile Lys Lys Asp Lys Glu Pro Glu Gly Pro Ala Gln Ala Ala Val Ala
                485                 490                 495

Ser Gly Cys Leu Thr Arg His Ala Ala Arg Glu His Arg Gln Asn Pro
                500                 505                 510

Val Arg Gly Ala His Ser Gln Gly Glu Ser Ser Pro Cys Thr Tyr Ile
                515                 520                 525

Thr Arg Arg Ser Val Arg Thr Arg Thr Asn Leu Lys Glu Ala Ser Asp
                530                 535                 540

Ile Lys Leu Glu Pro Asn Thr Leu Asn Gly Tyr Lys Ser Ser Val Thr
545                 550                 555                 560

Glu Pro Cys Pro Asp Ser Gly Glu Gln Leu Gln Pro Ala Pro Val Leu
                565                 570                 575

Gln Glu Glu Glu Leu Ala His Gly Thr Ala Gln Lys Gly Glu Ala Lys
                580                 585                 590

Cys His Lys Ser Asp Thr Gly Met Ser Lys Lys Ser Arg Gln Gly
                595                 600                 605

Lys Leu Val Lys Gln Phe Ala Lys Ile Glu Glu Ser Thr Pro Val His
        610                 615                 620

Asp Ser Pro Gly Lys Asp Asp Ala Val Pro Asp Leu Met Gly Pro His
625                 630                 635                 640

Ser Asp Gln Gly Glu His Ser Gly Thr Val Gly Val Pro Val Ser Tyr
                645                 650                 655

Thr Asp Cys Ala Pro Ser Pro Val Gly Cys Ser Val Val Thr Ser Asp
                660                 665                 670

Ser Phe Lys Thr Lys Asp Ser Phe Arg Thr Ala Lys Ser Lys Lys Lys
        675                 680                 685

Arg Arg Ile Thr Arg Tyr Asp Ala Gln Leu Ile Leu Glu Asn Asn Ser
        690                 695                 700

Gly Ile Pro Lys Leu Thr Leu Arg Arg Arg His Asp Ser Ser Ser Lys
705                 710                 715                 720

Thr Asn Asp Gln Glu Asn Asp Gly Met Asn Ser Ser Lys Ile Ser Ile
                725                 730                 735

Lys Leu Ser Lys Asp His Asp Asn Asn Leu Tyr Val Ala Lys
        740                 745                 750

Leu Asn Asn Gly Phe Asn Ser Gly Ser Gly Ser Ser Thr Lys Leu
        755                 760                 765

Lys Ile Gln Leu Lys Arg Asp Glu Glu Asn Arg Gly Ser Tyr Thr Glu
        770                 775                 780

Gly Leu His Glu Asn Gly Val Cys Cys Ser Asp Pro Leu Ser Leu Leu
785                 790                 795                 800

Glu Ser Arg Met Glu Val Asp Asp Tyr Ser Gln Tyr Glu Glu Glu Ser
                805                 810                 815

Thr Asp Asp Ser Ser Ser Ser Glu Gly Asp Glu Glu Asp Asp Tyr
                820                 825                 830
```

```
Asp Asp Asp Phe Glu Asp Asp Phe Ile Pro Leu Pro Pro Ala Lys Arg
        835                 840                 845

Leu Arg Leu Ile Val Gly Lys Asp Ser Ile Asp Ile Asp Ile Ser Ser
    850                 855                 860

Arg Arg Arg Glu Asp Gln Ser Leu Arg Leu Asn Ala
865                 870                 875

<210> SEQ ID NO 11
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial Sequence: primer
      specific for pACT

<400> SEQUENCE: 11
taccactaca atggatg                                                    17

<210> SEQ ID NO 12
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on sequence of AAP-2 protein

<400> SEQUENCE: 12

Glu Val Pro Lys Ser Thr Leu Glu Ser Glu Lys Pro Gly Ser Pro
1               5                  10                  15

<210> SEQ ID NO 13
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on sequence of AAP-2 protein

<400> SEQUENCE: 13

Ile Ser Ser Arg Lys Lys Lys Pro Asp Ser Pro Pro Lys Val Leu
1               5                  10                  15

<210> SEQ ID NO 14
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on sequence of AAP-2 protein

<400> SEQUENCE: 14

Thr Gly Ser Arg Thr Arg Gly Arg Trp Lys Tyr Ser Ser Asn Asp
1               5                  10                  15

<210> SEQ ID NO 15
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on sequence of AAP-3 protein

<400> SEQUENCE: 15
```

```
Ile Tyr Gln Arg Ser Gly Glu Arg Pro Val Thr Ala Gly Glu Glu
1               5                   10                  15

<210> SEQ ID NO 16
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on sequence of AAP-3 protein

<400> SEQUENCE: 16

Asp Glu Gln Val Pro Asp Ser Ile Asp Ala Arg Glu Ile Phe Asp
1               5                   10                  15

<210> SEQ ID NO 17
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on sequence of AAP-3 protein

<400> SEQUENCE: 17

Arg Ser Ile Asn Asp Pro Glu His Pro Leu Thr Leu Glu Glu Leu
1               5                   10                  15

<210> SEQ ID NO 18
<211> LENGTH: 10
<212> TYPE: PRT
<213> ORGANISM: Artificial Sequence
<220> FEATURE:
<221> NAME/KEY: misc_feature
<223> OTHER INFORMATION: Description of Artificial Sequence: Myc-tag

<400> SEQUENCE: 18

Glu Gln Lys Leu Ile Ser Glu Glu Asp Leu
1               5                   10
```